United States Patent [19]

Kumazawa et al.

[11] Patent Number: 5,478,835
[45] Date of Patent: Dec. 26, 1995

[54] TRICYCLIC COMPOUNDS AND INTERMEDIATES THEREOF

[75] Inventors: Toshiaki Kumazawa; Masashi Yanase, both of Shizuoka; Hiroyuki Harakawa, Numazu; Hiroyuki Obase, Mishima; Shoji Oda, Yokohama; Shiro Shirakura, Shizuoka; Koji Yamada, Susono; Kazuhiro Kubo, Shizuoka, all of Japan

[73] Assignee: Kyowa Hakko Kogyo Co., Ltd., Tokyo, Japan

[21] Appl. No.: 236,097

[22] Filed: May 2, 1994

Related U.S. Application Data

[62] Division of Ser. No. 989,906, Dec. 11, 1992, Pat. No. 5,340,807, which is a continuation of Ser. No. 823,456, Jan. 22, 1992, abandoned.

[30] Foreign Application Priority Data

Jan. 23, 1991 [JP] Japan .................. 3-006589

[51] Int. Cl.$^6$ ................ A61K 31/44; A61K 31/165; C07C 237/00; C07C 207/00
[52] U.S. Cl. .................. 514/290; 514/510; 514/562; 514/563; 514/599; 514/616; 514/617; 514/618; 514/619; 514/621; 514/622; 514/824; 546/93; 558/12; 558/13; 558/411; 558/414; 558/415; 558/416; 560/10; 560/18; 560/21; 560/22; 560/23; 560/25; 560/28; 562/427; 562/435; 562/437; 562/438; 562/453; 562/455; 564/74; 564/154; 564/155; 564/158; 564/162; 564/166; 564/167; 564/168; 564/169; 564/172; 564/180
[58] Field of Search ................ 564/74, 154, 155, 564/158, 162, 166, 167, 168, 169, 172, 180; 560/10, 18, 21, 22, 23, 25, 28; 562/427, 435, 437, 438, 453, 455; 546/93; 558/12, 13, 411, 414, 415, 416; 514/290, 510, 562, 563, 599, 616, 617, 618, 619, 621, 622, 824

[56] References Cited

U.S. PATENT DOCUMENTS

| | | | |
|---|---|---|---|
| 4,136,197 | 1/1979 | Hubner et al. | 424/319 |
| 4,489,090 | 12/1984 | DeVries et al. | 424/275 |
| 4,868,210 | 9/1989 | Trivedi | 514/539 |

OTHER PUBLICATIONS

Abou–Gharbia et al., Chemical Abstracts, vol. 91 (1979) 39211y.
J. Am. Chem. Soc. (1984) 106, 4175–80.
Heterocycles, vol. 12, No. 5 (1979) 637–45.
Chemical Abstracts, vol. 98 (1983) 89198q.
Chemical Abstracts, vol. 91 (1979) 39211y.

Primary Examiner—C. Warren Ivy
Assistant Examiner—Raymond Covington
Attorney, Agent, or Firm—Fitzpatrick, Cella, Harper & Scinto

[57] ABSTRACT

Disclosed is a tricyclic compound represented by the formula (I):

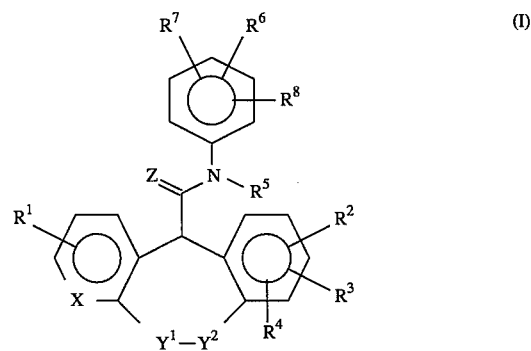

wherein each of $R^1$, $R^2$, $R^3$ and $R^4$ independently represents hydrogen, C1-6 alkyl, C1-6 alkoxy, C1-6 alkylthio, amino, C1-6 alkylamino, halogenated C1-6 alkyl, halogenated C1-6 alkoxy, halogen, nitro, cyano, carboxy, C1-6 alkoxycarbonyl, hydroxymethyl, $CR^9R^{10}CO_2R^{11}$ (wherein each of $R^9$, $R^{10}$ and $R^{11}$ independently represents hydrogen or C1-6 alkyl) or $CONR^{12}R^{13}$ (wherein each of $R^{12}$ and $R^{13}$ independently represents hydrogen or C1-6-alkyl); $R^5$ represents hydrogen or C1-6 alkyl; each of $R^6$, $R^7$ and $R^8$ independently represents hydrogen, C1-6 alkyl, hydroxy, C1-6 alkoxy, C1-6 alkanoyloxy, C1-6 alkylthio, thiocyanato or halogen; X represents CH or N; $Y^1$-$Y^2$ represents $CH_2$-O, $CH_2$-$S(O)_n$, (wherein n represents 0, 1, or 2), $CH_2CH_2$, CH=CH or $CON(R^{14})$ (wherein $R^{14}$ represents hydrogen or C1-6 alkyl) and Z represents oxygen or sulfur, or a pharmaceutically acceptable salt thereof. The compound possesses an acyl coenzyme A: cholesterol acyltransferase-inhibiting activity, and thus are expected to have preventive and therapeutic effects on hyperlipemia and arteriosclerosis.

11 Claims, No Drawings

TRICYCLIC COMPOUNDS AND INTERMEDIATES THEREOF

This application is a division of application Ser. No. 07/989,906, filed Dec. 11, 1992, U.S. Pat. No. 5,540,807 which is a continuation of application Ser. No. 07/823,456, filed Jan. 22, 1992, now abandoned.

BACKGROUND OF THE INVENTION

The present invention relates to tricyclic compounds and intermediates thereof with a side chain having an anilino moiety having an acyl coenzyme A: cholesterol acyltransferase (hereafter referred to as ACAT) inhibiting activity. The compounds are useful for the treatment of hyperlipemia and arteriosclerosis.

Myocardial infarction or cerebral infarction caused by arteriosclerosis has been ranked as high mortality in advanced countries, along with cancer. It has thus been desired to develop a medicine for the treatment of arteriosclerosis. Based on the results of many epidemiological investigations, it has already been pointed out that hypercholesterolemia is one of risk factors of arteriosclerosis. It has been reported that development of arteriosclerosis is prevented by reducing cholesterol level in blood serum, inter alia, cholesterol level with low density lipoprotein (LDL).

Cholesterol is supplied in vivo by biosynthesis and absorption. Compounds which inhibit biosynthesis and absorption might reduce cholesterol level in blood serum. As compounds having an activity of inhibiting absorption, nicotinic acid derivatives and sterols originated from plants are known. However, their activity is not sufficient.

Cholesterol is absorbed on epithelial cells of the intestine in its free form, then esterified by ACAT, included in chylomicron, and transported to liver by blood stream in chylomicron form. ACAT plays an important role in accumulation of cholesterol in liver. ACAT is also involved in transformation of macrophage to foam cell. ACAT is thought to cause progression of arteriosclerosis [J. Lipid Res., 26, 647 (1985); Nippon Rinsho (Clinic in Japan), 47, 554 (1989)]. Compounds which inhibit ACAT might inhibit the absorption of cholesterol and accumulation of cholesterol in liver. Therefore, these effects accelerate excretion of cholesterol and consequently reduce cholesterol level in blood serum. Furthermore, such compounds inhibit the formation of foam cells and are thus expected to be effective for the treatment of hyperlipemia and arteriosclerosis.

Compounds represented by formula (A) which possess an ACAT inhibitory activity are disclosed in U.S. Pat. No. 4,489,090.

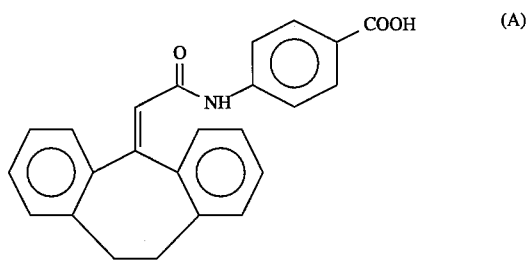

It is also described in Heterocycles, 12, 637 (1979) that compounds represented by formula (B):

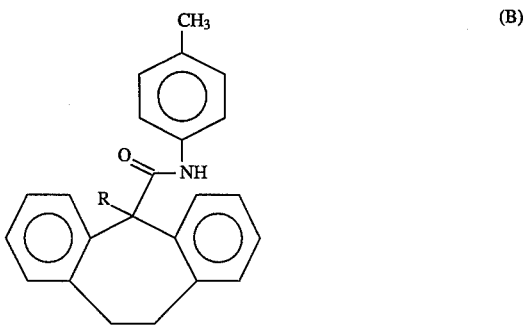

wherein R represents ethoxy or chlorine, have an antileukemia activity and antispasmodic activity.

The compounds represented by the formula (C):

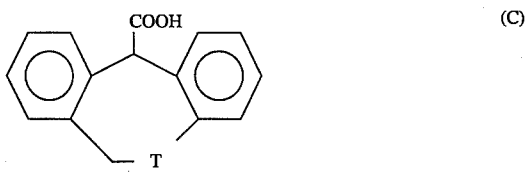

wherein T represents oxygen was described in Czech. CS., 202, 336. [Chem. Abst., 98, 89198q (1983)] and wherein T represents $CH_2$ was described in J. Am. Chem. Soc., 106. 4175 (1984).

SUMMARY OF THE INVENTION

An object of the present invention is to provide tricyclic compounds with a side chain having anilino moiety which are useful for the treatment of hyperlipemia and arteriosclerosis, and intermediates thereof.

The present invention relates to a tricyclic compound represented by formula (I):

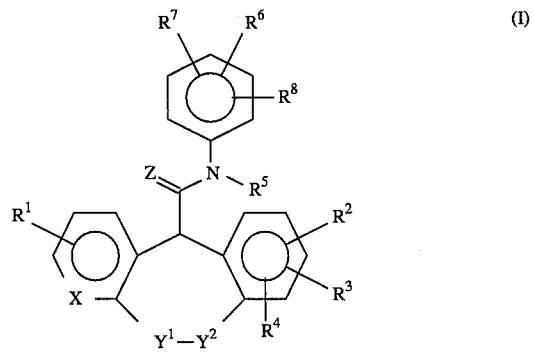

wherein each of $R^1$, $R^2$, $R^3$ and $R^4$ and independently represents hydrogen, lower alkyl, lower alkoxy, lower alkylthio, amino, lower alkylamino, halogenated lower alkyl, halogenated lower alkoxy, halogen, nitro, cyano, carboxy, lower alkoxycarbonyl, hydroxymethyl, $CR^9R^{10}CO_2R^{11}$ (wherein each of $R^9$, $R^{10}$ and $R^{11}$ independently represents hydrogen or lower alkyl) or $CONR^{12}R^{13}$ (wherein each of $R^{12}$ and $R^{13}$ independently represents hydrogen or lower alkyl); represents hydrogen or lower alkyl; each of $R^6$, $R^7$ and $R^8$ independently represents hydrogen, lower alkyl, hydroxy, lower alkoxy, lower alkanoyloxy, lower alkylthio, thiocyanato or halogen; X represents CH or N; $Y^1$-$Y^2$ represents CH$_2$-O, CH$_2$-S(O)n (wherein n represents 0, 1 or 2), CH$_2$CH$_2$, CH=CH or CON(R$^{14}$) (wherein R$^{14}$ represents hydrogen or lower alkyl) and Z represents oxygen or sulfur, and a pharmaceutically acceptable salt thereof, as well as an intermediate thereof represented by formula (IIa):

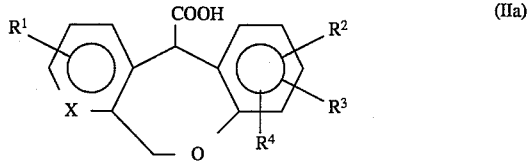

wherein each of R$^1$, R$^2$, R$^3$ and R$^4$ independently represents hydrogen, lower alkyl, lower alkoxy, lower alkylthio, amino, lo lower alkylamino, halogenated lower alkyl, halogenated lower alkoxy, halogen, nitro, cyano, carboxy, lower alkoxycarbonyl, hydroxymethyl CR$^9$R$^{10}$CO$_2$R$^{11}$ (wherein each of R$^9$, R$^{10}$ and R$^{11}$ independently represents hydrogen or lower alkyl) or CONR$^{12}$R$^{13}$ (wherein each of R$^{12}$ and R$^{13}$ independently represents hydrogen or lower alkyl); and X represents CH or N.

in the lower alkanoyloxy refers to a straight or branched chain alkanoyl having 1 to 6 carbon atoms such as formyl, acetyl, propionyl, butyryl, isobutyryl, valeryl, pivaloyl, etc. The halogen includes, for example, fluorine, chlorine, bromine and iodine. The alkyl moiety in the halogenated lower alkyl and halogenated lower alkoxy has the same significance as defined above, which is independently substituted with 1 to 6 halogens and the halogenated alkyl moiety includes, for example, trifluoromethyl, pentafluoroethyl, etc.

As the pharmaceutically acceptable salt of Compound (I), mention may be made of pharmaceutically acceptable acid addition salts, for example, inorganic acid salts such as hydrochlorides, sulfates, phosphates etc. and organic acid salts such as maleates, fumarates, citrates, etc.; pharmaceutically acceptable alkali metal salts such as lithium salts, sodium salts and potassium salts; pharmaceutically acceptable alkali earth metal salts such as calcium salts and magnesium salts, and pharmaceutically acceptable ammonium salts.

Processes for producing Compound (I) and Intermediate (IIa) are described below.

Process A

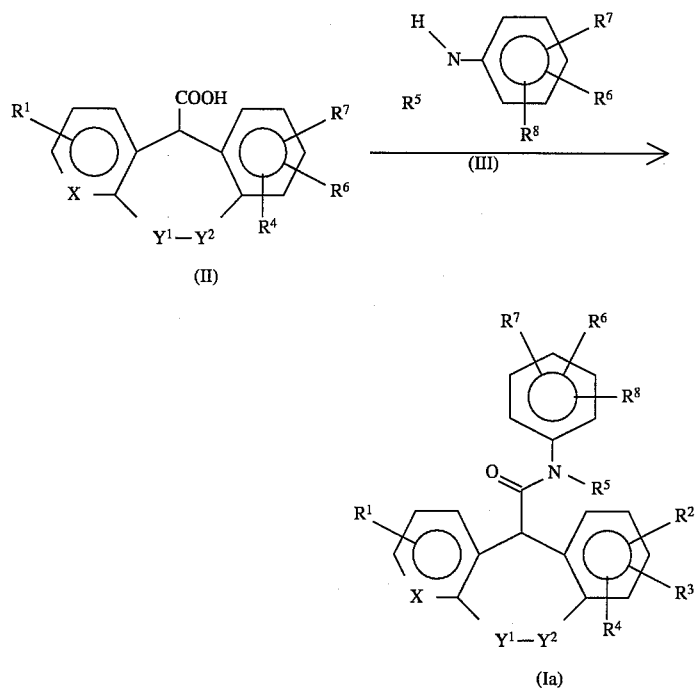

wherein X, Y$^1$-Y$^2$, R$^1$, R$^2$, R$^3$, R$^4$, R$^5$, R$^6$, R$^7$ and R$^8$ have the same significances as previously defined.

DETAILED DESCRIPTION OF THE INVENTION

The compound represented by formula (I) is referred to as Compound (I); and hereafter the same shall apply to other compounds of other formulae.

In the definitions of groups in formulae (I) and (IIa), the alkyl moiety in the lower alkyl, lower alkoxy, lower alkylthio, lower alkoxycarbonyl and lower alkylamino means a straight or branched chain alkyl having 1 to 6 carbon atoms such as methyl, ethyl, propyl, isopropyl, butyl, isobutyl, sec-butyl, tert-butyl, pentyl, hexyl, etc. The alkanoyl moiety Compound (Ia) which is Compound (I) wherein Z is oxygen can be obtained by condensing a reactive carboxylic acid (II) with an aniline derivative (III) in a conventional manner.

Aniline derivative (III) is reacted with a carboxylic acid reactive derivative such as an acid halide or a mixed acid anhydride, etc. derived from the reactive carboxylic acid (II) or with the carboxylic acid (II) using 1,3-dicyclohexylcarbodiimide or 2-chloro-1-methylpyridinium iodine, etc. as a condensing agent.

Compound (Ia) can be prepared by reacting Compound (II) with 1 to 20 equivalents of a halogenating agent such as thionyl chloride, oxalyl chloride, phosphorus pentachloride, phosphorus oxychloride, phosphorus tribromide, etc. in the absence of a solvent or in an inert solvent, e.g., dichloromethane or toluene at −80° to 60° C. for 5 minutes to 24 hours to obtain an acid halide, and then reacting the acid halide with 1 to 10 equivalents of Compound (III) in an inert solvent such as dichloromethane or toluene, if necessary, in the presence of an equimolar amount to a large excess of a base such as triethylamine or pyridine, further if necessary, in the presence of a catalyst such as 4-(N,N-dimethylamino)pyridine, etc. in a catalytic amount at an appropriate temperature of from −78° C. to the boiling point of a solvent used for 5 minutes to 24 hours.

Process B

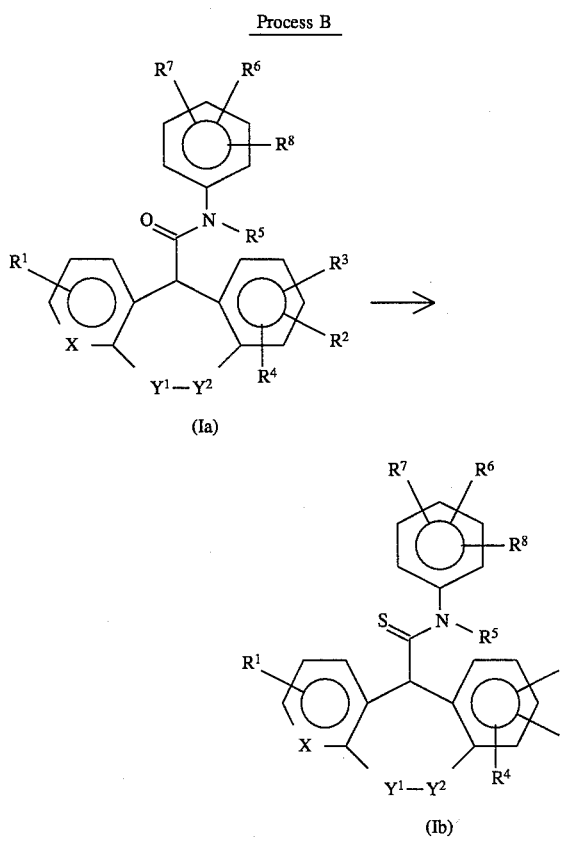

wherein X, $Y^1$-$Y^2$, $R^1$, $R^2$, $R^3$, $R^4$, $R^5$, $R^6$, $R^7$ and $R^8$ have the same significances as previously defined.

Compound (Ib) which is Compound (I) wherein Z is sulfur, can be obtained by reacting Compound (Ia) obtained by Process A with 1 to 5 equivalents of 2,4-bis(4-methoxyphenyl)-1,3-dithia-2,4-diphosphetane-2,4-disulfide (Lawesson's reagent) for 0.5 to 6 hours in a solvent such as benzene, toluene, xylene, etc., at an appropriate temperature of from 60° C. to the boiling point of a solvent used.

Process C

Compound (Ic) which is Compound (I) wherein at least one of $R^6$, $R^7$ and $R^8$ is hydroxy can be obtained by treating Compound (Id) which is Compound (I) wherein the corresponding group to each hydroxy group in Compound (Ic) is lower alkoxy, with boron tribromide or aluminium chloride. Compound (Id) is obtained using Compound (III) wherein at least one of the corresponding $R^6$, $R^7$ and $R^8$ is alkoxy in Process A.

Compound (Ic) can be obtained by reacting Compound (Id) with 1 to 5 equivalents of boron tribromide in a solvent such as dichloromethane or chloroform for 1 to 24 hours at an appropriate temperature of from −78° C. to room temperature and adding water to the reaction mixture.

Process D

Compound (Ie) which is Compound (I) wherein at least one of $R^1$, $R^2$, $R^3$, $R^4$, $R^6$, $R^7$ and $R^8$ is carboxy can also be obtained by hydrolyzing Compound (If) wherein the corresponding group is a lower alkoxycarbonyl. Compound (If) is obtained using Compound (II) and Compound (III) in either of which at least one of the corresponding $R^1$, $R^2$, $R^3$, $R^4$, $R^6$, $R^7$ and $R^8$ is lower alkoxycarbonyl in Process A.

Compound (Ie) can be obtained by hydrolyzation of Compound (If) in an aqueous organic solvent such as methanol, ethanol, tetrahydrofuran, 1,4-dioxane, etc. at an appropriate temperature of from room temperature to the boiling point of a solvent used, in the presence of 1 to 10 equivalents of lithium hydroxide, sodium hydroxide or potassium hydroxide.

Process E

Compound (Ig) which is Compound (I) wherein at least one of $R^1$, $R^2$, $R^3$ and $R^4$ is hydroxymethyl can also be obtained by reducing Compound (Ie) wherein at least one of the corresponding $R^1$, $R^2$, $R^3$ and $R^4$ is carboxymethyl in Process D.

Compound (Ig) can be obtained by reacting Compound (Ie) with 1 to 2 equivalents of ethyl chloroformate in a solvent such as ether, tetrahydrofuran and dimethylformamide, at an appropriate temperature of from 0° C. to room temperature in the presence of 1 to 2 equivalents of triethylamine or pyridine for 1 to 24 hours, and adding 1 to 2 equivalents of sodium borohydride thereto. The mixture was allowed to stand at an appropriate temperature of from 0° C. to room temperature for 1 to 12 hours.

Process F

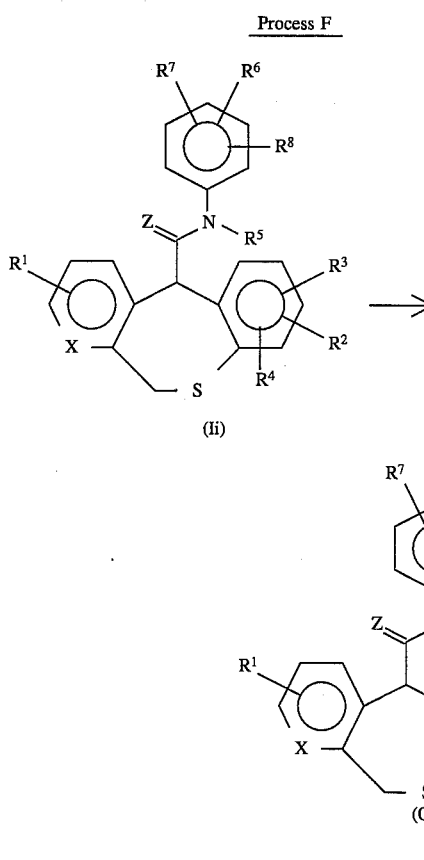

wherein m represents 1 or 2 and X, Z, $R^1$, $R^2$, $R^3$, $R^4$, $R^5$, $R^6$, $R^7$ and $R^8$ have the same significances as previously defined.

Compound (Ih), which is Compound (I) wherein $y^1$-$y^2$ represents —$CH_2$—S(O)m— wherein m represents 1 or 2 can be prepared by treating Compound (Ii) wherein $Y^1$-$Y^2$ represents —$CH_2$—S— with an appropriate oxidizing agent, for example, hydrogen peroxide, sodium metaperiodate, m-chloroperbenzoic acid, etc. Compound (Ii) is obtained using Compound (II) wherein $Y^1$-$Y^2$ is $CH_2S$ in Process A.

Compound (Ih) can be obtained by treating Compound (Ii) with 1 to 5 equivalents of m-chloroperbenzoic acid in dichloromethane in an appropriate temperature of from −78° C. to room temperature for 15 minutes to 6 hours.

Process G

Compound (Ij) which is Compound (I) wherein at least one of $R^1$, $R^2$, $R^3$ and $R^4$ is amino can be obtained by reducing Compound (Ik) wherein the corresponding group is nitro. Compound (Ik) is obtained using Compound (II) wherein at least one of the corresponding $R^1$, $R^2$, $R^3$ and $R^4$ is nitro Compound (Ij) can be obtained by reducing Compound (Ik) in an aqueous organic solvent such as methanol, ethanol, etc. at an appropriate temperature of from room temperature to the boiling point of a solvent used, in the presence of 2 to 10 equivalents of iron in the presence of a catalytic amount of ferric chloride.

Process H

Compound (Im) which is Compound (I) wherein at least one of $R^1$, $R^2$, $R^3$ and $R^4$ is lower alkylamino can be obtained by alkylating Compound (Ij) wherein the corresponding group is amino.

Compound (Im) can be obtained by reacting Compound (Ij) with 1 to 5 equivalents of sodium cyanoborohydride and 1 to 20 equivalents of the corresponding aldehyde in a solvent such as methanol or ethanol at an appropriate temperature of from 0° C. to room temperature under weakly acidic conditions.

In Process A, the starting Compound (IIa) which is Compound (II) wherein $Y^1$-$Y^2$ is $CH_2$-O prepared by the following method.

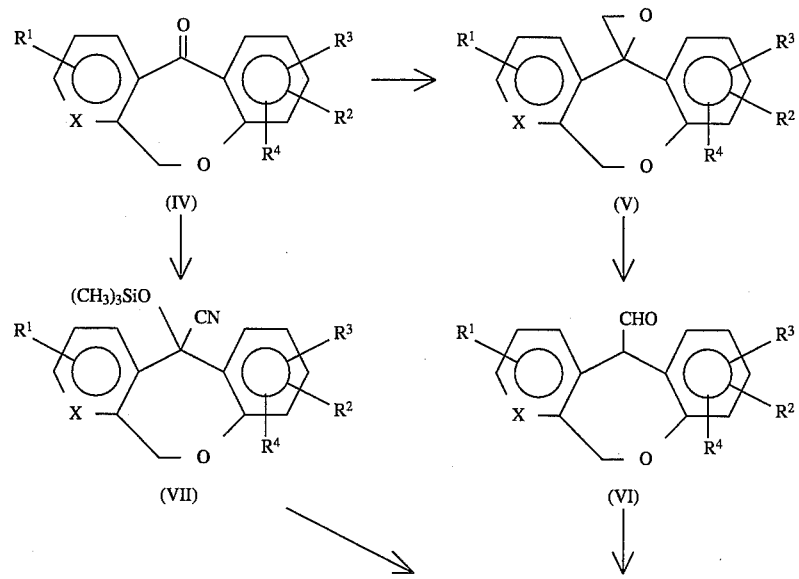

-continued

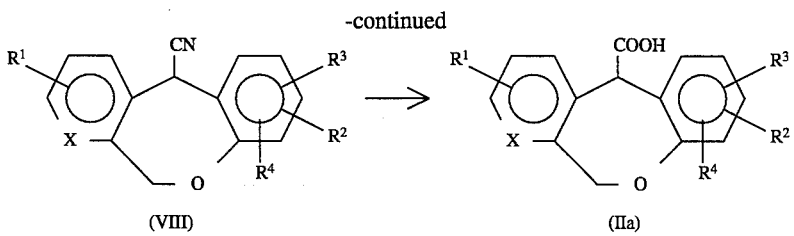

wherein X, $R^1$, $R^2$, $R^3$ and $R^4$ have the same significances as previously defined.

Compound (IV) prepared by the known method [West German Patent No. 1,294,970] or by its modified method is reacted with the ylide prepared by treating trimethylsulfonium iodide with 1 to 2 equivalents of sodium hydride, in a solvent mixture of dimethylsulfoxide and tetrahydrofuran at an appropriate temperature of from −78° C. to room temperature for 1 to 12 hours to give Compound (V). Compound (V) is reacted with a catalytic amount of Lewis acid, e.g., boron trifluoride-ether complex at an appropriate temperature of from −78° C. to 0° C. for 10 minutes to 6 hours in dichloromethane and the resulting mixture is treated with water to give Compound (VI). Compound (VI) can be converted into Compound (IIa) by conventional oxidation using as an oxidizing agent, for example, chromic oxide or potassium permanganate. For example, Compound (IIa) can be obtained by reacting Compound (VI) with an excess of Jones' reagent in acetone at an appropriate temperature of from −60° to 0° C.

Furthermore, Compound (IV) is reacted with 1 to 5 equivalents of trimethylsilylnitrile in dichloromethane at room temperature for 6 to 72 hours in the presence of a catalytic amount of zinc iodide and 10 to 100 wt. % of molecular sieve to give Compound (VII). Compound (VII) is treated under reflux in hydrochloric acid-acetic acid (1:1) for 1 to 6 hours in the presence of an equimolar amount of stannous chloride to give Compound (IIa).

Compound (IIa) may also be obtained by treating Compound (VIII) prepared by the known method (Japanese Published Unexamined Patent Application No. 35178/75) or by its modified method with a mineral acid, for example, hydrochloric acid, sulfuric acid or phosphoric acid at 60 to 120° C. for 1 to 12 hours, if necessary, in the presence of acetic acid.

Compound (IIb) which is Compound (II) wherein $Y^1$-$Y^2$ represents $CH_2$-S, $CH_2CH_2$, CH=CH or CON($R^{14}$) (wherein $R^{14}$ has the same significance as previously defined) can be prepared by a similar method to that for producing Compound (IIa) and by the known methods [Chem. Abst., 98, 89198q (1983), J. Am. Chem. Soc., 106, 4175 (1984)] or by their modified method.

The intermediates and the desired compounds in the processes described above can be isolated and purified by methods for purification conventionally used in organic synthetic chemistry, for example, filtration, extraction, washing, drying, concentration, recrystallization, various chromatographies, etc. The intermediates can be served for the next reaction without any particular purification.

Where it is desired to obtain the salts of Compound (I), the salts may be purified as they are when the product is obtained in a salt form. Where the product is obtained in a free form, the product is dissolved or suspended in an appropriate solvent and an acid or a base is added to the solution or suspension to form its salt.

Compound (I) and its pharmaceutically acceptable salt thereof may be present in the form of adducts with water or various solvents. These adducts are also included in the present invention.

Further, the present invention includes all possible stereoisomers and a mixture thereof.

Specific examples of Compound (I) obtained by the respective processes are shown in Table 1 and specific examples of the intermediates (IIa) are shown in Table 2.

TABLE 1

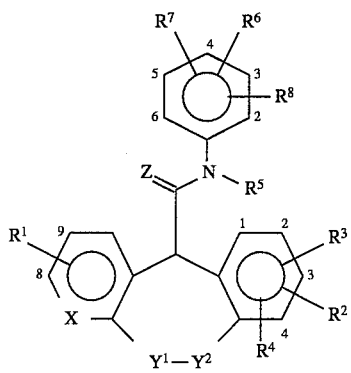

| Compound No | X | Y¹—Y² | Z | R¹ | R² | R³ | R⁴ | R⁵ | R⁶ | R⁷ | R⁸ |
|---|---|---|---|---|---|---|---|---|---|---|---|
| 1 | CH | CH₂O | O | H | 2-Me | H | H | H | H | H | H |
| 2 | CH | CH₂O | O | H | 2-Me | H | H | H | 2-Me | 6-Me | H |
| 3 | CH | CH₂O | O | H | 2-Me | H | H | H | 2-Et | 6-Et | H |
| 4 | CH | CH₂O | O | H | 2-Me | H | H | H | 2-iPr | 6-iPr | H |
| 5 | CH | CH₂O | O | H | 2-Me | H | H | H | 2-iPr | H | H |
| 6 | CH | CH₂O | O | H | 2-Me | H | H | H | 2-Cl | 6-Cl | H |
| 7 | CH | CH₂O | O | H | 2-Me | H | H | H | 2-Br | 6-Br | H |
| 8 | CH | CH₂O | O | H | 2-Me | H | H | H | 2-Me | 6-Cl | H |
| 9 | CH | CH₂O | O | H | 2-Me | H | H | H | 2-Me | 4-Me | 6-Me |
| 10 | CH | CH₂O | O | H | 2-Me | H | H | H | 2-OMe | 4-OMe | 6-OMe |
| 11 | CH | CH₂O | O | H | 2-Et | H | H | H | 2-iPr | 6-iPr | H |
| 12 | CH | CH₂O | O | H | 2-iPr | H | H | H | 2-Me | 6-Me | H |
| 13 | CH | CH₂O | O | H | 2-iPr | H | H | H | 2-Et | 6-Et | H |
| 14 | CH | CH₂O | O | H | 2-tBu | H | H | H | 2-Me | 6-Me | H |
| 15 | CH | CH₂O | O | H | H | H | H | H | 2-iPr | 6-iPr | H |
| 16 | CH | CH₂O | O | H | 2-F | H | H | H | 2-iPr | 6-iPr | H |
| 17 | CH | CH₂O | O | H | 2-Cl | H | H | H | 2-iPr | 6-iPr | H |
| 18 | CH | CH₂O | O | H | 2-Br | H | H | H | 2-iPr | 6-iPr | H |
| 19 | CH | CH₂O | O | H | 2-I | H | H | H | 2-iPr | 6-iPr | H |
| 20 | CH | CH₂O | O | H | 2-CF₃ | H | H | H | 2-iPr | 6-iPr | H |
| 21 | CH | CH₂O | O | H | 2-Me | 4-Br | H | H | 2-iPr | 6-iPr | H |
| 22 | CH | CH₂O | O | H | 2-OMe | H | H | H | 2-iPr | 6-iPr | H |
| 23 | CH | CH₂O | O | H | 2-CN | H | H | H | 2-iPr | 6-iPr | H |
| 24 | CH | CH₂O | O | H | 2-COOMe | H | H | H | 2-iPr | 6-iPr | H |
| 25 | CH | CH₂O | O | H | 2-COOH | H | H | H | 2-iPr | 6-iPr | H |
| 26 | CH | CH₂O | O | H | 2-CH₂OH | H | H | H | 2-iPr | 6-iPr | H |
| 27 | CH | CH₂O | O | H | 2-Br | H | H | H | 2-Et | 6-Et | H |
| 28 | CH | CH₂O | O | H | 3-Br | H | H | H | 2-Cl | 6-Cl | H |
| 29 | CH | CH₂O | O | H | 3-Br | H | H | H | 2-iPr | 6-iPr | H |
| 30 | CH | CH₂O | O | H | 2-Me | H | H | H | 2-iPr | 4-SMe | 6-iPr |
| 31 | CH | CH₂O | O | H | 2-Me | H | H | H | 2-iPr | 4-SCN | 6-iPr |
| 32 | CH | CH₂S | O | H | 2-Br | H | H | H | 2-iPr | 6-iPr | H |
| 33 | CH | CH₂O | O | 9-Br | H | H | H | H | 2-iPr | 6-iPr | H |
| 34 | CH | CH₂O | O | 9-Br | 2-Me | H | H | H | 2-iPr | 6-iPr | H |
| 35 | CH | CH₂O | O | 9-Br | 2-Br | H | H | H | 2-iPr | 6-iPr | H |
| 36 | CH | CH₂O | S | H | 2-Me | H | H | H | 2-iPr | 6-iPr | H |
| 37 | CH | CH₂O | S | H | 2-Br | H | H | H | 2-iPr | 6-iPr | H |
| 38 | N | CH₂O | O | H | H | H | H | H | 2-iPr | 6-iPr | H |
| 39 | CH | CH₂O | O | H | 2-Br | H | H | E | 2-Cl | 6-Cl | H |
| 40 | CH | CH₂O | O | H | 2-Br | H | H | H | 2-F | 4-F | H |
| 41 | N | CH₂O | O | H | 2-OMe | H | H | H | 2-iPr | 6-iPr | H |
| 42 | N | CH₂O | O | H | 2-Br | H | H | H | 2-iPr | 6-iPr | H |
| 43 | CH | CH₂O | O | H | 2-Br | H | H | Me | H | H | H |
| 44 | CH | CH₂O | O | H | 2-Br | H | H | H | 2-iPr | 4-SMe | 6-iPr |
| 45 | CH | CH₂O | O | H | 2-tBu | H | H | H | 2-Cl | 6-Cl | H |
| 46 | CH | CH₂O | O | H | 2-NO₂ | H | H | H | 2-iPr | 6-iPr | H |
| 47 | CH | CH₂O | O | H | 2-CONMe₂ | H | H | H | 2-iPr | 6-iPr | H |
| 48 | CH | CH₂O | O | H | 2-Me | 3-Me | H | H | 2-iPr | 6-iPr | H |
| 49 | CH | CH₂O | O | H | 1-Me | 4-Me | H | H | 2-iPr | 6-iPr | H |
| 50 | CH | CH₂O | O | H | 1-Me | 4-Me | H | H | 2-Et | 6-Et | H |
| 51 | CH | CH₂O | O | H | 2-Me | 4-CO₂Me | H | H | 2-iPr | 6-iPr | H |
| 52 | CH | CH₂O | O | H | 2-Me | 4-CO₂H | H | H | 2-iPr | 6-iPr | H |
| 53 | CH | CH₂O | O | H | 2-Br | 4-NO₂ | H | H | 2-iPr | 6-iPr | H |
| 54 | CH | CH₂O | O | H | 2-Br | 4-NH₂ | H | H | 2-iPr | 6-iPr | H |
| 55 | CH | CH₂O | O | H | 2-Br | 4-NMe₂ | H | H | 2-iPr | 6-iPr | H |
| 56 | CH | CH₂O | O | H | 1-Me | 2-Br | 3-Me | H | 2-iPr | 6-iPr | H |
| 57 | CH | CH₂O | O | H | 1-Me | 2-Br | 3-Me | H | 2-Et | 6-Et | H |
| 58 | CH | CH₂O | O | H | 1-Me | 2-Br | 3-Me | H | 2-Me | 6-Me | H |

TABLE 1-continued

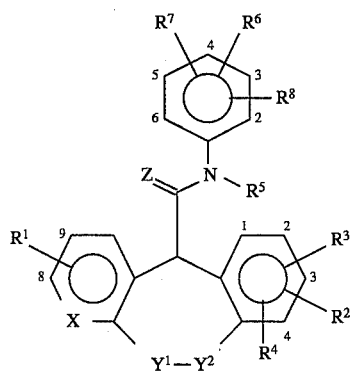

| Compound No | X | Y¹—Y² | Z | R¹ | R² | R³ | R⁴ | R⁵ | R⁶ | R⁷ | R⁸ |
|---|---|---|---|---|---|---|---|---|---|---|---|
| 59 | CH | CH₂O | O | H | 1-Me | 2-Me | 4-Cl | H | 2-iPr | 6-iPr | H |
| 60 | CH | CH₂O | O | H | 2-Br | H | H | H | 2-iPr | 6-iPr | H |
| 61 | CH | CH₂O | O | H | 2-Br | H | H | H | 2-iPr | 6-iPr | H |
| 62 | CH | CH₂O | O | H | 1-Me | 3-Me | H | H | 2-iPr | 6-iPr | H |
| 63 | CH | CH₂O | O | H | 1-Me | 3-Me | H | H | 2-Et | 6-Et | H |
| 64 | CH | CH₂O | O | H | 1-Me | 4-Cl | H | H | 2-iPr | 6-iPr | H |
| 65 | CH | CH₂O | O | H | 2-SMe | H | H | H | 2-iPr | 6-iPr | H |
| 66 | CH | CH₂O | O | 10-Me | 2-Br | H | H | H | 2-iPr | 6-iPr | H |
| 67 | CH | CH₂CH₂ | O | H | H | H | H | H | 2-iPr | 6-iPr | H |
| 68 | CH | CH₂CH₂ | O | H | 2-Me | H | H | H | 2-iPr | 6-iPr | H |
| 69 | CH | CH₂CH₂ | O | H | 2-Br | H | H | H | 2-iPr | 6-iPr | H |
| 70 | CH | CH=CH | O | H | H | H | H | H | 2-iPr | 6-iPr | H |
| 71 | CH | CON(Me) | O | H | 2-Br | H | H | H | 2-iPr | 6-iPr | H |

In the table, Me, Et, iPro and tBu represent methyl, ethyl, isopropyl and tert-butyl, respectively.

The numbering of the compounds shown in the table corresponds to the numbering of Examples hereinafter.

The number which designates the position of each substituent represents the positional number in the figure. Thus, it might be different from the number given in the nomenclature.

TABLE 2

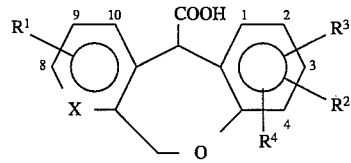

| Compound No (Example) | X | R¹ | R² | R³ | R⁴ |
|---|---|---|---|---|---|
| A (39) | CH | H | 2-Me | H | H |
| B (40) | CH | H | 2-Et | H | H |
| C (41) | CH | H | 2-iPr | H | H |
| D (42) | CH | H | 2-tBu | H | H |
| E (43) | CH | H | H | H | H |
| F (44) | CH | H | 2-F | H | H |
| G (45) | CH | H | 2-Cl | H | H |
| H (46) | CH | H | 2-Br | H | H |
| J (47) | CH | H | 2-CN | H | H |
| K (48) | CH | H | 3-Br | H | H |
| L (49) | CH | H | 2-COOMe | H | H |
| M (50) | CH | H | 2-I | H | H |
| N (51) | CH | H | 2-CF₃ | H | H |
| P (52) | CH | H | 2-OMe | H | H |
| Q (53) | CH | H | 2-Me | 4-Br | H |
| R (54) | CH | 9-Br | H | H | H |
| S (55) | CH | 9-Br | 2-Me | H | H |

TABLE 2-continued

| Compound No (Example) | X | R¹ | R² | R³ | R⁴ |
|---|---|---|---|---|---|
| T (56) | CH | 9-Br | 2-Br | H | H |
| U (57) | N | H | H | H | H |
| W (58) | N | H | 2-OMe | H | H |
| X (59) | N | H | 2-Br | H | H |
| Y (60) | CH | H | 2-Br | H | H |
| Z (61) | CH | H | 2-Br | H | H |
| AA (62) | CH | H | 2-NO₂ | H | H |
| AB (63) | CH | H | 2-Me | 3-Me | H |
| AC (64) | CH | H | 1-Me | 4-Me | H |
| AD (65) | CH | H | 2-Me | 4-COOMe | H |
| AE (66) | CH | H | 2-Br | 4-NO₂ | H |
| AF (67) | CH | H | 1-Me | 2-Br | 3-Me |
| AG (68) | CH | H | 1-Me | 2-Me | 4-Cl |
| AH (69) | CH | H | 2-SMe | H | H |
| AI (70) | CH | 10-Me | 2-Br | H | H |
| AJ (71) | CH | H | 1-Me | 3-Me | H |
| AK (72) | CH | H | 1-Me | 4-Cl | H |

In the table, Me, Et, iPro and tBu represent methyl, ethyl, isopropyl and tert-butyl, respectively.

The pharmacological activities of Compound (I) are explained below. The same shall apply as in table 1 with respect of the positional number.

TEST EXAMPLE 1

Test for Acute Toxicity

Groups of 3 male ddy strain mice weighing 20±1 g were used. The test compounds were orally administered. Seven days after administration, the mortality was observed and the minimum lethal dose (MLD) was determined. The results are given in Table 3.

TABLE 3

| Compound No. | Acute Toxicity (MLD) (mg/kg) |
|---|---|
| 3 | >300 |
| 4 | >300 |
| 5 | >300 |
| 16 | >300 |
| 17 | >300 |
| 18 | >300 |
| 20 | >300 |
| 23 | >300 |
| 24 | >300 |
| 27 | >300 |
| 28 | >300 |
| 29 | >300 |
| 32 | >300 |

TEST EXAMPLE 2

Test for ACAT Inhibitory Activity

The test for ACAT inhibitory activity was performed by a modified method of the method of Brecher et al. Biochim. Biophys. Acta, 617, 458 (1980)]. 10 µl of a solution of each test compound (final concentration of the test compound: $10^{-6}$M)-in methanol was added to 180 µl of 0.1M phosphate buffer containing 0.1 mg protein of microsome fraction prepared from rabbit liver, 2 mM dithiothreitol and 1.7 mg of bovine serum albumin.. Furthermore [14C] oleoyl coenzyme A was added to the mixture followed by incubation at 37° C. for 10 minutes. After 4 ml of chloroform/methanol (2:1) containing [$^3$H] cholesterol oleate was added to the reaction mixture, the chloroform layer was evaporated under reduced pressure to dryness. The residue was fractionated by silica gel thin layer chromatography (a developing solvent: petroleum ether/diethyl ether/acetic acid (170:30:1)). The radioactivity of the cholesterol ester spot was determined by a liquid scintillation counter. The radioactivity for each test compound was calculated by the difference between the radioactivity with the microsome fraction and the radioactivity without the microsome fraction. The radioactivity of control was determined in a similar manner without any test compound. The ACAT inhibitory activity of each test compound was calculated according to the following equation.

$$\text{Inhibition rate (\%)} = \frac{\left(\begin{array}{c}\text{radioactivity}\\\text{of control}\end{array}\right) - \left(\begin{array}{c}\text{radioactivity of}\\\text{test compound}\end{array}\right)}{\left(\begin{array}{c}\text{radioactivity}\\\text{of control}\end{array}\right)} \times 100$$

The results are shown in Table 4.

TABLE 4

| Compound No. | Inhibiting rate (%) $10^{-6}$M |
|---|---|
| 2 | 66 |
| 3 | 77 |
| 4 | 98 |
| 5 | 56 |
| 16 | 81 |
| 17 | 94 |
| 18 | 100 |
| 20 | 84 |
| 23 | 69 |
| 21 | 90 |
| 27 | 80 |
| 28 | 52 |
| 29 | 86 |
| 30 | 78 |
| 32 | 88 |
| 39 | 91 |
| 42 | 91 |
| 44 | 95 |
| 48 | 96 |
| 49 | 97 |
| 50 | 93 |
| 51 | 99 |
| 53 | 100 |
| 55 | 100 |
| 56 | 99 |
| 57 | 98 |
| 59 | 100 |
| 60 | 99 |
| 61 | 92 |
| 62 | 100 |
| 64 | 100 |
| 68 | 99 |
| 69 | 98 |

TEST EXAMPLE 3

Inhibition effect on serum cholesterol level in hamster with dietary hyperlipemia Golden hamster (SLC, male, age of 6 weeks) was made free access to feed containing 2% cholesterol for 3 days. Each test compound was suspended in olive oil and orally administered once a day in a dose of 30 mg/kg during the feeding. (A: Test Group administered with the test compound, B: Control Group administered with olive oil only). In Group C, feed free from cholesterol was fed for 3 days. On the fourth day, blood sample was collected from the descending aorta under pentobarbital anesthesia and cholesterol level in serum was determined. The total cholesterol level in serum of each group was determined and the inhibition rate for the test compound was calculated according to the following equation.

$$\text{Inhibition rate (\%)} = \frac{B-A}{B-C} \times 100$$

The results are shown in Table 5.

TABLE 5

| Compound No. | Inhibition Rate (%) |
|---|---|
| 4 | 70 |
| 18 | 114 |
| 20 | 63 |
| 21 | 67 |
| 32 | 67 |

Compound (I) or its pharmaceutically acceptable salt may be administered singly as they are, but it is generally preferred that these compounds be administered in the form of various pharmaceutical preparations. These pharmaceutical preparations can be used for animals and human beings.

The most effective administrative route is chosen from oral and parenteral administration such as intrarectal, topical, intranasal, intraocular, intrabuccal, subcutaneous, intramuscular and intravenous routes, etc.

As the form of administration, mention may be made of a capsule, a tablet, a granule, a powder, a syrup, an emulsion, a suppository, an injection, etc.

A liquid preparation suitable for oral administration, for example, an emulsion and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as p-hydroxybenzoic acid esters, etc.; flavors such as strawberry flavor, pepper mint, etc. Further a capsule, a tablet, a powder and a granule, etc. can be prepared using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as an aliphatic ester, etc.; a plasticizer such as glycerine, etc.

A preparation suitable for parenteral administration is a sterile aqueous preparation containing compound (I), and preferably isotonic to blood of recipient. For example, with an injection, a solution for injection is prepared using carriers composed of a saline solution, a glucose solution or a mixture of saline and glucose solution.

A preparation for rectal administration is provided as a suppository using conventional carriers, for example, cacao fat, hydrogenated fat or hydrogenated fat carboxylic acid, etc.

Further these parenteral preparations may also be added with one or more auxiliary components such as a diluent, a flavour, an antiseptic (including an antioxidant), an excipient, a disintegrator, a lubricant, a binder, a surfactant, a plasticizer and the like.

Effective dose and number of administration of Compound (I) or pharmaceutically acceptable salt thereof vary depending upon administration route, age, body, weight and conditions of patients. In general, daily dose for oral administration is 1 µg to 300 mg/kg and daily dose for parenteral administration is 0.1 µg to 30 mg/kg. The number of administration is once to several times a day; the dosage may vary according to the various conditions.

Hereafter, the present invention is described by referring to Examples and Reference Examples below.

Example 1

6,11-Dihydro-2-methyl-N-phenyldibenz[b,e]-oxepin-11-carboxamide (Compound 1)

After 1.0 g of 6,11-dihydro-2-methyldibenz[b,e]-oxepin-11-carboxylic acid (Compound A) obtained in Example 39 was dissolved in 10 ml of dichloromethane, 5.0 g of oxalyl chloride was added to the solution Under ice cooling. The mixture was stirred for 4 hours. The reaction solution was concentrated under reduced pressure and the residue was dissolved in 5 ml of dichloromethane. The solution was dropwise added to a solution of 0.44 g of aniline, 1.19 g of triethylamine and a catalytic amount of 4-(N,N-dimethyl)-aminopyridine in 8 ml of dichloromethane under ice cooling. After stirring at room temperature for 9 hours, the reaction mixture was diluted with dichloromethane. After washing with 1N hydrochloric acid, saturated sodium hydrogencarbonate aqueous solution and saturated aqueous sodium chloride solution successively, the organic solution was dried over anhydrous magnesium sulfate. After concentration under reduced pressure, the resulting residue was purified by column chromatography on silica gel [eluent: hexane-ethyl acetate (4:1)]. Recrystallization of the crude product from ethyl acetate-hexane gave 1.25 g of Compound 1 as colorless needles.

Melting Point: 129.0°–130.0° C. IR (KBr tablet: $cm^{-1}$): 3274, 1645, 1598, 1500, 1440, 1225 NMR (δ, ppm; $CDCl_3$): 2.31(s, 3H), 4.73(s, 1H), 4.96 and 5.49(q, 2H, AB type, J=14.5Hz), 6.93–7.46(m, 12H), 7.93 (brs, 1H)

Example 2

6,11-Dihydro-2-methyl-N-(2,6-dimethylphenyl)-dibenz[b,e]-oxepin-11-carboxamide (Compound 2)

The similar procedures as in Example 1 were repeated except using 0.57 g of 2,6-dimethylaniline in place of aniline, to obtain 1.68 g of Compound 2.

Melting Point: 162.0–163.0° C. IR (KBr tablet: $cm^{-1}$): 3250, 3238, 1650, 1642, 1518, 1232 NMR (δ, ppm; $CDCl_3$): 2 02(s, 6H), 2.31 (s, 3H), 4.08 (s, 1H), 5.01 and 5.53(q, 2H, AB type, J=14.8 Hz), 6.93–7.53 (m, 11H)

Example 3

N-(2,6-Diethylphenyl)-6,11-dihydro-2-methyl-dibenz[b,e]-oxepin-11-carboxamide (Compound 3)

The similar procedures as in Example 1 were repeated except using 1.47 g of Compound A and 0.78 g of 2,6-diethylaniline in place of aniline to obtain 1.34 g of Compound 3.

Melting Point: 201.5°–203.0° C. IR (KBr tablet: $cm^{-1}$): 3268, 2962, 1650, 1642, 1500, 12231 NMR (δ, ppm; $CDCl_3$): 0.93(t, 6H, J=7.5Hz), 2.32(s, 3H), 2.34 (q, 4H, J=7.5Hz), 4.84 (s, 1H), 5.04 and 5.50(q, 2H, AB type, J=14.8 Hz) , 6.92–7.66 (m, 11H)

Example 4

6,11-Dihydro-N-(2,6-diisopropylphenyl)-2-methyl-dibenz[b,e]-oxepin-11-carboxamide (Compound 4)

The similar procedures as in Example 1 were repeated except using 1.20 g of Compound A and 1.00 g of 2,6-diisopropylaniline in place of aniline to obtain 1.85 g of Compound 4.

Melting Point: 166.5°–167.0° C. IR (KBr tablet: cm): 3280, 2958, 1650, 1528, 1503, 1231 NMR (δ, ppm; $CDCl_3$): 0.96 (d, 6H, J=6.8 Hz) , 1.01 (d, 6H, J=6.6 Hz), 2.32 (s, 3H), 2.63–2.79 (m, 2H) , 4.86 (s, 1H), 5.04 and 5.48 (q, 2H, AB type, J=14.7 Hz), 6.98–7.64 (m, 11H)

Example 5

6,11-Dihydro-N-(2-isopropylphenyl)-2-methyl-dibenz[b,e]-oxepin-11-carboxamide (Compound 5)

The similar procedures as in Example 1 were repeated except using 1.0 g of Compound A and 0.63 g of 2-isopropylaniline in place of aniline to obtain 1.84 g of Compound 5.

Melting Point: 180.0°–181.0° C. IR (KBr tablet: cm$^{-1}$): 3262, 2958, 1667, 1512, 1494, 1454, 1227 NMR (δ, ppm; CDCl$_3$): 0.99 (d, 6H, J=6.8 Hz), 2.32(s, 3H), 2.42–2.57 (m, 1H), 4.78(s, 1H), 4.95 and 5.48 (q, 2H, AB type, J=14.4Hz), 6.90–7.48 (m, 12H)

Example 6

N-(2,6-Dichlorophenyl)-6,11-dihydro-2-methyl-dibenz[b,e]-oxepin-11-carboxamide (Compound 6)

The similar procedures as in Example 1 were repeated except using 1.0 g of Compound A and 0.76 g of 2,6-dichloroaniline in place of aniline to obtain 1.38 g of Compound 6.

Melting Point: 156.0°–157.0° C. IR (KBr tablet: cm$^{-1}$): 3236, 1662, 1510, 1504, 1485, 1228 NMR (δ, ppm; CDCl$_3$): 2.31 (s, 3H), 4.78 (s, 1H), 4.95 and 5.65 (q, 2H, AB type, J=14.1Hz), 6.97–7.64 (m, 11H)

Example 7

N-(2,6-Dibromophenyl)-6,11-dihydro-2-methyl-dibenz[b,e]-oxepin-11-carboxamide (Compound 7)

The similar procedures as in Example 1 were repeated except using 1.40 g of Compound A and 1.28 g of 2,6-dibromoaniline in place of aniline to obtain 1.46 g of Compound 7.

Melting Point: 183.5°–184.5° C. IR (KBr tablet: cm$^{-1}$): 3238, 1660, 1510, 1502, 1444, 1228 NMR (δ, ppm; CDC13): 2.31 (s, 3H), 4.79 (s, 1H), 4.96 and 5.70(q, 2H, AB type, J=14.4 Hz), 6.88–7.68 (m, 11H)

Example 8

N-(2-Chloro-6-methylphenyl)-6,11-dihydro-2-methyldibenz[b,e]-oxepin-11-carboxamide (Compound 8)

The similar procedures as in Example 1 were repeated except using 1.40 g of Compound A and 0.72 g of 2-chloro-6-methylaniline in place of aniline to obtain 1.54 g of Compound 8.

Melting Point: 160.0°–161.0° C. IR (KBr tablet: cm$^{-1}$): 3242, 1660, 1643, 1530, 1511, 1502, 1228 NMR (δ, ppm; CDCl$_3$): 2.16 (s, 3H), 2.31 (s, 3H), 4.77 (s, 1H), 4.98 and 5.59 (q, 2H, AB type, J=14.5Hz), 7.00–7.55 (m, 11H)

Example 9

6,11-Dihydro-2-methyl-N-(2,4,6-trimethylphenyl)-dibenz[b,e]-oxepin-11-carboxamide (Compound 9)

The similar procedures as in Example 1 were repeated except using 1.47 g of Compound A and 0.71 g of 2,4,6-trimethylaniline in place of aniline to obtain 1.20 g of Compound 9.

Melting Point: 148.0°–149.0 ° C. IR (KBr tablet: cm$^{-1}$): 3254, 1648, 1502, 1227 NMR (δ, ppm; CDCl$_3$): 1.98 (s, 6H), 2.20 (s, 3H), 2.31 (s, 3H), 4.79 (s, 1H), 5.00 and 5.54 (q, 2H, AB type, J=14.7 Hz), 6.79(s, 2H), 7.01–7.49 (m, 8H)

Example 10

6,11-Dihydro-2-methyl-N-(2,4,6-trimethoxyphenyl)-dibenz[b,e]-oxepin-11-carboxamide (Compound 10)

The similar procedures as in Example 1 were repeated except using 2.32 g of Compound A and 1.85 g of 2,4,6-trimethoxyaniline in place of aniline to obtain 1.56 g of Compound 10 as amorphous.

IR (KBr tablet: cm$^{-1}$): 3390, 2936, 1693, 1600, 1501, 1468, 1227, 1153 NMR (δ, ppm; CDCl$_3$): 2.26 (s, 3H), 3.70 (s, 6H), 3.73 (s, 3H), 4.70 (s, 1H), 4.83 and 5.80 (q, 2H, AB type, J=13.7 Hz), 6.06 (s, 2H), 6.75–7.34 (m, 8H)

Example 11

2-Ethyl-6,11-dihydro-N-(2,6-diisopropylphenyl)-dibenz[b,e]-oxepin-11-carboxamide (Compound 11)

The similar procedures as in Example 1 were repeated except using 1.40 g of 2-ethyl-6,11-dihydrodibenz[b,e]oxepin-11-carboxylic acid (Compound B) obtained in Example 40 in place of Compound A and 0.83 g of 2,6-diisopropylaniline in place of aniline to obtain 1.40 g of Compound 11.

Melting Point: 154.5°–155.5° C. IR (KBr tablet: cm$^{-1}$): 3282, 2962, 1650, 1524, 1503, 1232 NMR (δ, ppm; CDCl$_3$): 0.95 (d, 6H, J=6.8 Hz), 1.00 (d, 6H, J=6.8 Hz), 1.23 (3H, t, J=7.5 Hz), 2.51–2.77 (m, 4H), 4.90 (s, 1H), 5.06 and 5.49 (q, 2H, AB type, J=14.7 Hz), 6.98–7.69 (m, 11H)

Example 12

6,11-Dihydro-2-isopropyl-N-(2,6-dimethylphenyl)-dibenz[b,e]-oxepin-11-carboxamide (Compound 12)

The similar procedures as in Example 1 were repeated except using 2.34 g of 6,11-dihydro-2-isopropyldibenz[b,e]oxepin-11-carboxylic acid (Compound C) obtained in Example 41 in place of Compound A and 0.73 g of 2,6-dimethylaniline in place of aniline to obtain 1.18 g of Compound 12.

Melting Point: 149.5°–150.5° C. IR (KBr tablet: cm$^{-1}$): 3250, 2950, 1656, 1649, 1503 NMR (δ, ppm; CDCl$_3$): 1.24 (d, 6H, J=6.8 Hz), 2.02 (s, 6H), 2.74–2.97 (m, 1H), 4.85 (s, 1H), 5.03 and 5.55 (q, 2H, AB type, J=14.7Hz), 6.99–7.55 (m, 11H)

Example 13

N-(2,6-Diethylphenyl)-6,11-dihydro-2-isopropyl-dibenz[b,e]-oxepin-11-carboxamide (Compound 13)

The similar procedures as in Example 1 were repeated except using 2.34 g of Compound C in place of Compound A and 0.90 g of 2,6-diethylaniline in place of aniline to obtain 1.26 g of Compound 13.

Melting Point: 169.5°–170.5° C. IR (KBr tablet: cm$^{-1}$): 3276, 2960, 1656, 1649, 1524, 1503, 1231 NMR (δ, ppm; CDCl$_3$): 0.92 (t, 6H, J=7.6 Hz), 1.24 (d, 6H, J=6.8 Hz), 2.32 (q, 4H, J=7.5 Hz), 2.75–2.93 (m, 1H), 4.89 (s, 1H), 5.06 and 5.51 (q, 2H, AB type, J=14.6 Hz), 6.98–7.70 (m, 11H)

Example 14

2-(tert-Butyl)-6,11-dihydro-N-(2,6-dimethylphenyl)-dibenz[b,e]-oxepin-11-carboxamide (Compound 14)

The similar procedures as in Example 1 were repeated except using 1.50 g of 2-(tert-butyl)-6,11-dihydrodibenz[b,e]oxepin-11-carboxylic acid (Compound D) obtained in Example 42 in place of Compound A and 0.61 g of 2,6-dimethylaniline in place of aniline to obtain 1.36 g of Compound 14.

Melting Point: 116.0°–117.0° C. IR (KBr tablet: cm$^{-1}$): 3268, 2960, 1651, 1644, 1510, 1503, 1233 NMR (δ, ppm; CDCl$_3$): 1.31 (s, 9H), 2.03 (s, 6H), 4.86 (s, 1H), 5.02 and 5.57 (q, 2H, AB type, J=14.7 Hz), 6.99–7.56 (m, 11H)

Example 15

6,11-Dihydro-N-(2,6-diisopropylphenyl)dibenz[b,e]-oxepin-11-carboxamide (Compound 15)

The similar procedures as in Example 1 were repeated except using 1.92 g of 6,11-dihydrodibenz[b,e]-oxepin-11-carboxylic acid (Compound E) obtained in Example 43 in place of Compound A and 1.65 g of 2,6-diisopropylaniline in place of aniline to obtain 2.0 8 g of Compound 15.

Melting Point: 168.0°–169.0° C. IR (KBr tablet: cm$^{-1}$): 3298, 2956, 1658, 1518 NMR (δ, ppm; CDCl$_3$): 0.96 (d, 6H, J=6.8 Hz), 1.01 (d, 6H, J=6.8 Hz), 2.63–2.78 (m, 2H), 4.92 (s, 1H), 5.06 and 5.53(q, 2H, AB type, J=14.7 Hz), 6.98–7.58 (m, 12H)

Example 16

2-Fluoro-6,11-dihydro-N-(2,6-diisopropylphenyl)-dibenz[b,e]-oxepin-11-carboxamide (Compound 16)

The similar procedures as in Example 1 were repeated except using 2.17 g of 2-fluoro-6,11-dihydrodibenz[b,e]oxepin-11-carboxylic acid (Compound F) obtained in Example 44 in place of Compound A and 1.79 g of 2,6-diisopropylaniline in place of aniline to obtain 3.37 g of Compound 16.

Melting Point: 158.0°–159.0° C. IR (KBr tablet: cm$^{-1}$): 3280, 2960, 1658, 1650, 1495 NMR (δ, ppm; CDCl$_3$): 0.97 (d, 6H, J=6.8 Hz), 1.01 (d, 6H, J=6.8 Hz), 2.63–2.78 (m, 2H), 4.86 (s, 1H), 5.06 and 5.48 (q, 2 H, AB type, J=14.9 Hz), 6.96–7.58 (m, 11H)

Example 17

2-Chloro-6,11-dihydro-N-(2,6-diisopropylphenyl)-dibenz[b,e]-oxepin-11-carboxamide (Compound 17)

The similar procedures as in Example 1 were repeated except using 2.0 g of 2-chloro-6,11-dihydrodibenz[b,e]oxepin-11-carboxylic acid (Compound G) obtained in Example 45 in place of Compound A and 1.95 g of 2,6-diisopropylaniline in place of aniline to obtain 2.44 g of Compound 17.

Melting Point: 185.0°–186.0° C. IR (KBr tablet: cm$^{-1}$): 3230, 1661, 1505, 1500, 1228 NMR (δ, ppm; CDCl$_3$): 1.01 (d, 6H, J=6.8 Hz), 1.03 (d, 6H, J=7.0 Hz), 2.67–2.82 (m, 2H), 4.83 (s, 1H), 5.02 and 5.55(q, 2H, AB type, J=14.7 Hz), 6.98–7.50 (m, 11H)

Example 18

2-Bromo-6,11-dihydro-N-(2,6-diisopropylphenyl)-dibenz[b,e]-oxepin-11-carboxamide (Compound 18)

The similar procedures as in Example 1 were repeated except using 1.70 g of 2-bromo-6,11-dihydrodibenz[b,e]oxepin-11-carboxylic acid (Compound H) obtained in Example 46 in place of Compound A and 1.13 g of 2,6-diisopropylaniline in place of aniline to obtain 2.49 g of Compound 18.

Melting Point: 191.5°–193.0° C. IR (KBr tablet: cm$^{-1}$): 3282, 2960, 1656, 1650, 1525, 1484, 1233 NMR (δ, ppm; CDCl$_3$): 1.01 (d, 6H, J=6.8 Hz), 1.04 (d, 6H, J=6.8 Hz), 2.67–2.83 (m, 2H), 4.82 (s, 1H), 5.01 and 5.56(q, 2H, AB type, J=14.6 Hz), 6.92–7.55 (m, 11H)

Example 19

6,11-Dihydro-2-iodo-N-(2,6-diisopropylphenyl)-dibenz[b,e]-oxepin-11-carboxamide (Compound 19)

The similar procedures as in Example 1 were repeated except using 1.0 g of 2-iodo-6,11-dihydrodibenz[b,e]-oxepin-11-carboxylic acid (Compound M) obtained in Example 50 in place of Compound A and 0.54 g of 2,6-diisopropylaniline in place of aniline to obtain 1.32 g of Compound 19.

Melting Point: 201.0°–202.0° C. IR (KBr tablet: cm$^{-1}$): 3284, 2958, 1656, 1651, 1524, 1480, 1233 NMR (δ, ppm; CDCl$_3$): 1.02 (d, 6H, J=6.8 Hz), 1.04 (d, 6H, J=6.8 Hz), 2.68–2.83 (m, 2H), 4.80 (s, 1H), 5.00 and 5.57 (q, 2H, AB type, J=14.5 Hz), 6.83 (d, 1H, J=8.3 Hz), 7.00–7.73(m, 10H)

Example 20

6,11-Dihydro-N-(2,6-diisopropylphenyl)-2-trifluoromethyldibenz[b,e]oxepin-11-carboxamide (Compound 20)

The similar procedures as in Example 1 were repeated except using 3.35 g of 6,11-dihydro-2-trifluoromethyldibenz[b,e]oxepin-11-carboxylic acid (Compound N) obtained in Example 51 in place of Compound A and 1.93 g of 2,6-diisopropylaniline in place of aniline to obtain 4.22 g of Compound 20.

Melting Point: 200.0°–201.0° C. IR (KBr tablet: cm$^{-1}$): 3284, 2964, 1658, 1649, 1525, 1333, 1263 NMR (δ, ppm; CDCl$_3$): 1.04 (d, 12H, J=7.0 Hz), 2.70–2.85 (m, 2H), 4.92 (s, 1H), 5.00 and 5.72 (q, 2H, AB type, J=14.3 Hz), 7.01–7.65 (m, 11H)

Example 21

4-Bromo-6,11-dihydro-N-(2,6-diisopropylphenyl)-2-methyldibenz[b,e]oxepin-11-carboxamide (Compound 21)

The similar procedures as in Example 1 were repeated except using 2.11 g of 4-bromo-6,11-dihydro-2-methyldibenz[b,e]oxepin-11-carboxylic acid (Compound Q) obtained in Example 53 in place of Compound A and 1.01 g of 2,6-diisopropylaniline in place of aniline to obtain 1.52 g of Compound 21.

Melting Point: 172.0°–173.0° C. IR (KBr tablet: cm$^{-1}$): 3282, 2960, 1651, 1528, 1475 NMR (δ, ppm; CDCl$_3$): 0.96 (d, 6H, J=7.0 Hz), 1.04 (d, 6H, J=7.5 Hz), 2.31 (s, 3H), 2.58–2.82 (m, 2H), 4.85 (s, 1H), 5.10 and 5.50(q, 2H, AB type, J=14.8 Hz), 6.99–7.56 (m, 10H)

Example 22

6,11-Dihydro-N-(2,6-diisopropylphenyl)-2-methoxy-dibenz[b,e]-oxepin-11-carboxamide (Compound 22)

The similar procedures as in Example 1 were repeated except using 6.54 g of 6,11-dihydro-2-methoxydibenz[b,e]-oxepin-11-carboxylic acid (Compound P) obtained in Example 52 in place of Compound A and 4.30 g of 2,6-diisopropylaniline in place of aniline to obtain 7.96 g of Compound 22.

Melting Point: 152.0°–153.0° C. IR (KBr tablet: cm$^{-1}$): 3292, 2960, 1656, 1651, 1521, 1500, 1226 NMR (δ, ppm; CDCl$_3$): 0.94 (d, 6H, J=6.8 Hz), 0.99 (d, 6H, J=6.8 Hz), 2.61–2.76 (m, 2H), 3.80 (s, 3H), 4.88 (s, 1H), 5.07 and 5.43(q, 2H, AB type, J=15.2 Hz), 6.79–7.56(m, 10H), 7.83 (brs, 1H)

Example 23

2-Cyano-6,11-dihydro-N-(2,6-diisopropylphenyl)-dibenz[b,e]-oxepin-11-carboxamide (Compound 23)

The similar procedures as in Example 1 were repeated except using 1.41 g of 2-cyano-6,11-dihydrodibenz[b,e]oxepin-11-carboxylic acid (Compound J) obtained in Example 47 in place of Compound A and 0.85 g of 2,6-diisopropylaniline in place of aniline to obtain 1.32 g of Compound 23.

Melting Point: 175.0°–176.0° C. IR (KBr tablet: cm$^{-1}$): 3302, 2960, 2226, 1643, 1500, 1239 NMR (δ, ppm; CDCl$_3$): 1.06 (d, 12H, J=6.8 Hz), 2.68–2.92 (m, 2H), 4.85 (s, 1H), 4.96 and 5.80 (q, 2H, AB type, J=14.0Hz), 6.82 (brs, 1H), 6.98-7.67 (m, 10H)

Example 24

6,11-Dihydro-N-(2,6-diisopropylphenyl)-2-methoxycarbonyldibenz[b,e]oxepin-11-carboxamide (Compound 24)

The similar procedures as in Example 1 were repeated except using 1.10 g of 6,11-dihydro-2-methoxycarbonyldibenz[b,e]oxepin-11-carboxylic acid (Compound L) obtained in Example 49 in place of Compound A and 0.79 g of 2,6-diisopropylaniline in place of aniline to obtain 1.63 g of Compound 24.

Melting Point: 169.5°–170.5° C. IR (KBr tablet: cm$^{-1}$): 3280, 2964, 1721, 1650, 1500, 1258 NMR (δ, ppm; CDCl$_3$): 1.05 (d, 12H, J=7.3 Hz), 2.72–2.87 (m, 2H), 3.90 (s, 3H), 4.92 (s, 1H), 4.98 and 5.75 (q, 2H, AB type, J=13.7 Hz), 6.99–7.45 (m, 9H), 7.92 (dd, 1H, J=8.6 and 2.2 Hz), 8.09 (d, 1H, J=2.2 Hz)

Example 25

2-Carboxy-6,11-dihydro-N-(2,6-diisopropylphenyl)-dibenz[b,e]-oxepin-11-carboxamide (Compound 25)

After 0.58 g of 6,11-dihydro-N-(2,6-diisopropylphenyl)-2-methoxycarbonyldibenz[b,e]oxepin-11-carboxamide (Compound 24) obtained in Example 24 was dissolved in 24 ml of methanol, 6 ml of 5 N sodium hydroxide was added to the solution. The mixture was heated under reflux for 5 minutes. After completion of the reaction, the mixture was cooled to room temperature and 4N hydrochloric acid was added thereto to adjust pH to 3. The mixture was extracted with ethyl acetate. After washing with saturated sodium hydroxide aqueous solution, the organic layer was dried over anhydrous magnesium sulfate and concentrated under reduced pressure to dryness to obtain 0.52 g of Compound 25.

Melting Point: 289.0°–290.0° C. IR (KBr tablet: cm$^{-1}$): 3280, 2962, 2868, 1690, 1651, 1608, 1501, 1259, 1236 NMR (δ, ppm; CDCl$_3$): 1.02 (d, 12H, J=6.8 Hz), 2.61–2.93 (m, 2H), 5.18 (s, 1H), 4.84 and 6.26 (q, 2H, AB type, J=13 Hz), 6.89–7.87 (m, 10H), 8.14 (brs, 1H), 8.46 (brs, 1H)

EXAMPLE 26

6,11-Dihydro-2-hydroxymethyl-N-(2,6-diisopropylphenyl)dibenz[b,e]oxepin-11-carboxamide (Compound 26)

After 1.33 g of 2-ocarboxy-6,11-dihydro-N-( 2,6-diisopropylphenyl)dibenz[b,e]oxepin-11-carboxamide (Compound 25) obtained in Example 25 was dissolved in 10 ml of tetrahydrofuran, 1.0 ml of triethylamine and 0.39 g of ethyl chloroformate were added to the solution under ice cooling. The mixture was stirred at room temperature for 12 hours. Then 0.57 g of sodium borohydride was slowly added to the reaction mixture under ice cooling. After stirring at room temperature for 6 hours, saturated aqueous sodium chloride solution was added and the mixture was extracted with ethyl acetate. After drying over anhydrous magnesium sulfate, the organic layer was concentrated under reduced pressure. The resulting residue was purified by silica gel column chromatography [eluent: hexane-ethyl acetate (2:1)]. The crude crystal was recrystallized from ethyl acetate-hexane to obtain 1.08 g of Compound 26 as white needles.

Melting Point: 157.0°–158.0° C. IR (KBr tablet: cm$^{-1}$): 3318, 3286, 2962, 1659, 1650, 1526, 1502, 1232 NMR (δ, ppm; CDCl$_3$): 0.97(d, 6H, J=6.6 Hz), 1.02 (d, 6H, J=6.8 Hz), 1.75 (brs, 1H), 2.67–2.82(m, 2H), 4.62 (s, 2H), 4.89 (s, 1H), 5.03 and 5.54 (q, 2H, AB type, J=14.8 Hz), 6.99–7.45 (m, 11H)

Example 27

2-Bromo-N-(2,6-diethylphenyl)-6,11-dihydro-dibenz[b,e]oxepin-11-carboxamide (Compound 27)

The similar procedures as in Example 1 were repeated except using 1.37 g of Compound H obtained in Example 46 in place of Compound A and 0.59 g of 2,6-diethylaniline in place of aniline to obtain 1.14 g of Compound 27.

Melting Point: 234.5°–235.0° C. IR (KBr tablet: cm$^{-1}$): 3264, 2962, 1650, 1643, 1514, 1482, 1233 NMR (δ, ppm; CDCl$_3$): 0.98 (t, 6H, J=7.6 Hz), 2.37 (q, 4H, J=7.4 Hz), 4.80 (s, 1H), 5.01 and 5.57 (q, 2H, AB type, J=14.6 Hz), 6.92–7.55 (m, 11H)

Example 28

3-Bromo-N-(2,6-dichlorophenyl)-6,11-dihydro-dibenz[b,e]oxepin-11-carboxamide (Compound 28)

The similar procedures as in Example 1 were repeated except using 1.40 g of 3-bromo-6,11-dihydrodibenz[b,e]oxepin-11-carboxylic acid (Compound K) obtained in Example 48 in place of Compound A and 0.71 g of 2,6-dichloroaniline in place of aniline to obtain 1.01 g of Compound 28.

Melting Point: 169.5°–170.5° C. IR (KBr tablet: cm$^{-1}$): 3226, 1682, 1653, 1530, 1483, 1452, 1014 NMR (δ, ppm; CDCl$_3$): 4.79 (s, 1H), 4.94 and 5.73 (q, 2H, AB type, J=14.1 Hz), 7.08–7.46 (m, 11H)

Example 29

3-Bromo-6,11-dihydro-N-(2,6-diisopropylphenyl)-dibenz[b,e]-oxepin-11-carboxamide (Compound 29)

The similar procedures as in Example 1 were repeated except using 1.40 g of Compound K in place of Compound A and 0.78 g of 2,6-diisopropylaniline in place of aniline to obtain 1.54 g of Compound 29.

Melting Point: 170.5°–171.5° C. IR (KBr tablet: cm$^{-1}$): 3340, 2960, 1665, 1594, 1484, 1016 NMR (δ, ppm; CDCl$_3$): 1.00 (d, 6H, J=6.8 Hz), 1.03 (d, 6H, J=6.8 Hz), 2.65–2.80 (m, 2H), 4.86 (s, 1H), 5.02 and 5.57 (q, 2H, AB type, J=14.5 Hz), 7.00–7.56 (m, 11H)

Example 30

6,11-Dihydro-N-(2,6-diisopropyl-4-methylthiophenyl)-2-methyldibenz[b,e]oxepin-11-carboxamide (Compound 30)

The similar procedures as in Example 1 were repeated except using 1.12 g of Compound A and 1.18 g of 2,6-diisopropyl-4-methylthioaniline in place of aniline to obtain 1.70 g of Compound 30.

Melting Point: 125.5°–126.5° C. IR (KBr tablet: cm$^{-1}$): 3264, 2962, 1651, 1504 NMR (δ, ppm; CDCl$_3$): 0.94 (d, 6H, J=6.6 Hz), 1.00 (d, 6H, J=6.8 Hz), 2.32 (s, 3H), 2.43 (s, 3H), 2.59–2.74 (m, 2H), 4.85 (s, 1H), 5.04 and 5.49 (q, 2H, AB type, J=14.8 Hz), 6.96 (s, 2H), 7.04–7.60 (m, 8H)

Example 31

6,11-Dihydro-N-(2,6-diisopropyl-4-thiocyanatophenyl)-2-methyldibenz[b,e]oxepin-11-carboxamide (Compound 31)

The similar procedures as in Example 1 were repeated except using 1.12 g of Compound A and 1.24 g of 2,6-diisopropyl-4-thiocyanatoaniline in place of aniline to obtain 1.63 g of Compound 31.

Melting Point: 145.5°–146.5° C. IR (KBr tablet: cm$^{-1}$): 3245, 2960, 2150, 1650, 1500 NMR (δ, ppm; CDCl$_3$): 0.93 (d, 6H, J=6.2 Hz), 1.00 (d, 6H, J=6.4 Hz), 2.33 (s, 3H), 2.60–2.74 (m, 2H), 4.87 (s, 1H), 5.07 and 5.44(q, 2H, AB type, J=15.3 Hz), 7.08–7.54 (m, 9H), 7.82 (brs, 1H)

Example 32

2-Bromo-6,11-dihydro-N-(2,6-diisopropylphenyl)-dibenzo[b,e]thiepin-11-carboxamide (Compound 32)

The similar procedures as in Example 1 were repeated except using 1.70 g of 2-bromo-6,11-dihydrodibenzo[b,e]thiepin-11-carboxylic acid obtained in Reference Example 1 in place of Compound A and 0.90 g of 2,6-diisopropylaniline in place of aniline to obtain 1.42 g of Compound 32.

Melting Point: 189.0°–190.0° C. IR (KBr tablet: cm$^{-1}$): 3300, 2964, 1646, 1518, 1485, 1461 NMR (δ, ppm; CDCl$_3$): 1.05(d, 12H, J=6.8 Hz), 2.70–3.14 (m, 2H), 3.71 and 4.75 (q, 2H, AB type, J=15.1 Hz), 4.87(s, 1H), 6.83 (brs, 1H), 7.09–7.36 (m, 9H), 7.55 (d, 1H, J=2.0 Hz)

Example 33

9-Bromo-6,11-dihydro-N-(2,6-diisopropylphenyl)-dibenz[b,e]oxepin-11-carboxamide (Compound 33)

The similar procedures as in Example 1 were repeated except using 1.72 g of 9-bromo-6,11-dihydrodibenz[b,e]oxepin-11-carboxylic acid (Compound R) obtained in Example 54 in place of Compound A and 1.15 g of 2,6-diisopropylaniline in place of aniline to obtain 1.50 g of Compound 33.

Melting Point: 165.0°–166.0° C. IR (KBr tablet: cm$^{-1}$): 3270, 2958, 1657, 1487, 1317, 1230 NMR (δ, ppm; CDCl$_3$): 0.97 (d, 6H, J=6.6 Hz), 1.05 (d, 6H, J=6.6 Hz), 2.64–2.79 (m, 2H), 4.85 (s, 1H), 4.99 and 5.48 (q, 2H, AB type, J=14.5 Hz), 6.99–7.71 (m, 11H)

Example 34

9-Bromo-6,11-dihydro-N-(2,6-diisopropylphenyl)-2-methyldibenz[b,e]oxepin-11-carboxamide (Compound 34)

The similar procedures as in Example 1 were repeated except using 3.33 g of 9-bromo-6,11-dihydrodibenz[b,e]oxepin-11-carboxylic acid (Compound S) obtained in Example 55 in place of Compound A and 2.13 g of 2,6-diisopropylaniline in place of aniline to obtain 2.74 g of Compound 34.

Melting Point: 149.0°–151.0° C. IR (KBr tablet: cm$^{-1}$): 3254, 2955, 1644, 1515, 1316, 1224 NMR (δ, ppm; CDCl$_3$): 0.97 (d, 6H, J=6.6 Hz), 1.05 (d, 6H, J=6.6 Hz), 2.33 (s, 3H), 2.56–2.79(m, 2H), 4.79 (s, 1H), 4.97 and 5.43 (q, 2H, AB type, J=14.6 Hz), 6.97–7.70 (m, 10H)

Example 35

2,9-Dibromo-6,11-dihydro-N-(2,6-diisopropylphenyl)-dibenz[b,e]oxepin-11-carboxamide (Compound 35)

The similar procedures as in Example 1 were repeated except using 1.77 g of 2,9-dibromo-6,11-dihydrodibenz[b,e]oxepin-11-carboxylic acid (Compound T) obtained in Example 56 in place of Compound A and 1.56 g of 2,6-diisopropylaniline in place of aniline to obtain 0.3 g of Compound 35.

Melting Point: 202.0°–204.0° C. IR (KBr tablet: cm$^{-1}$): 3260, 2868, 1641, 1518, 1307, 1230 NMR (δ, ppm; CDCl$_3$): 1.00 (d, 6H, J=4.6 Hz), 1.08 (d, 6H, J=4.6 Hz), 2.59–2.89 (m, 2H), 4.76 (s, 1H), 4.95 and 5.51 (q, 2H, AB type, J=14.6 Hz), 6.93–7.66 (m, 10H)

Example 36

6,11-Dihydro-N-(2,6-diisopropylphenyl)-2-methyl-dibenz[b,e]oxepin-11-carbothioamide (Compound 36)

After 1.09 g of Compound 4 obtained in Example 4 was dissolved in 10 ml of toluene, 1.07 g of Lawesson's reagent was added to the solution. The mixture was heated under reflux for an hour. The reaction mixture was allowed to stand at room temperature, and concentrated under reduced pressure. The resulting residue was purified by silica gel column chromatography [eluent: hexane-ethyl acetate (2:1)] to obtain 1.46 g of a crude product. The crude product was recrystallized from ethyl acetate-hexane to obtain 1.09 g of Compound 36.

Melting Point: 140.0°–141.0° C. IR (KBr tablet: cm$^{-1}$): 3248, 2956, 1500, 1442, 1413, 1210 NMR (δ, ppm; CDCl$_3$): 0.72 (d, 3H, J=6.8 Hz), 0.88 (d, 3H, J=6.8 Hz), 1.00 (d, 3H, J=6.6 Hz), 1.04 (d, 3H, J=6.8 Hz), 2.34 (s, 3H), 2.34–2.47 (m, 2H), 5.09 and 5.39 (q, 2H, AB type, J=15.8 Hz), 5.55 (s, 1H), 7.10–7.71 (m, 10H), 9.87 (brs, 1H)

Example 37

2-Bromo-6,11-dihydro-N-(2,6-diisopropylphenyl)-dibenz[b,e]oxepin-11-carbothioamide (Compound 37)

The similar procedures as in Example 36 were repeated except using 0.97 g of 2-bromo-6,11-dihydro-N-(2,6-diisopropylphenyl)dibenz[b,e]oxepin-11-carboxamide obtained in Example 18 in place of Compound 4 to obtain 0.83 g of Compound 37.

Melting Point: 189.5°–191.0° C. IR (KBr tablet: cm$^{-1}$): 3270, 2962, 1504, 1495, 1479, 1404 NMR (δ, ppm; CDCl$_3$): 0.76 (d, 3H, J=6.8 Hz), 0.90 (d, 3H, J=6.8 Hz), 1.04 (d, 3H, J=6.8 Hz), 1.07 (d, 3H, J=6.8 Hz), 2.33–2.59 (m, 2H), 5.05 and 5.44 (q, 2H, AB type, J=14.9 Hz), 5.46 (s, 1H), 6.97–7.74 (m, 10H), 9.43 (brs, 1H)

Example 38

5,11-Dihydro-N-(2,6-diisopropylphenyl)benzoxepino-[3,4-b]pyridin-5-carboxamide (Compound 38)

The similar procedures as in Example 1 were repeated except using 0.55 g of 5,11-dihydrobenzoxepin[3,4-b]pyridin-5-carboxylic acid (Compound U) obtained in Example 57 in place of Compound A and 0.60 g of 2,6-diisopropylaniline in place of aniline to obtain 0.73 g of Compound 38.

Melting Point: 154.0°–155.0° C. IR (KBr tablet: cm$^{-1}$): 3282, 2962, 1650, 1587, 1494, 1222

NMR (δ, ppm; CDCl$_3$): 0.93 (d, 6H, J=1.5 Hz), 1.00 (d, 6H, J=1.5 Hz), 2.53–2.76 (m, 2H), 4.87 (s, 1H), 5.15 and 5.57 (q, 2H, AB type, J=16.0 Hz), 6.99–7.93 (m, 10H), 8.51 (dd, 1H, J=1.5 and 4.8 Hz)

Example 39

6,11-dihydro-2-methyldibenz[b,e]oxepin-11-carboxylic acid (Compound A)

In a nitrogen flow, 6.0 g of 60% oily sodium hydride was suspended in 500 ml of dimethylsulfoxide-tetrahydrofuran (1:1). After 30.6 g of trimethylsulfonium iodide was added to the suspension at −5° C., a solution of 22.4 g of 6,11-dihydro-2-methyldibenz[b,e]oxepin-11-one in 100 ml of dimethylsulfoxide-tetrahydrofuran (1:1) was dropwise added to the mixture. The mixture was stirred at room temperature for 10 hours. After 10 ml of water was dropwise added under ice cooling, 300 ml of water was added to the mixture followed by extraction with ether. After washing with saturated sodium chloride aqueous solution, the organic layer was dried over anhydrous magnesium sulfate and then evaporated under reduced pressure to dryness to obtain 22.8 g of 6,11-dihydro-2-methyldibenz[b,e]oxepin-11-spiro-2′-oxilane.

After 22.6 g of the compound described above was dissolved in 500 ml of dichloromethane, 1.2 ml of boron trifluoride ether complex was added to the solution under a nitrogen atmosphere followed by stirring at room temperature for 50 minutes. 10 ml of water was added to the reaction solution, and the resultant mixture was diluted with dichloromethane. The organic layer was washed with saturated sodium bicarbonate aqueous solution and saturated sodium chloride aqueous solution successively, dried over anhydrous sodium magnesium and evaporated to dryness under reduced pressure to obtain 21.9 g of 6,11-dihydro-2-methyldibenz[b,e]oxepin-11-carbaldehyde.

After 21.7 g of the compound described above was dissolved in 300 ml of acetone, an excess amount of Jones' reagent was added to the solution at −30° C. The mixture was stirred for 2.5 hours. The reaction solution was extracted with ethyl acetate. The organic layer was washed with water and extracted with saturated sodium bicarbonate aqueous solution three times. After adjusting pH to 2 with 4N hydrochloric acid, the aqueous layer was extracted with ethyl acetate. The organic layer was washed with saturated sodium chloride aqueous solution, dried over anhydrous magnesium sulfate and concentrated to dryness under reduced pressure to obtain 10.68 g of Compound A.

Melting Point: 183.0°–184.0° C. IR (KBr tablet: cm$^{-1}$): 3064, 2894, 1710, 1705, 1689, 1503 NMR (δ, ppm; CDCl$_3$): 2.27 (s, 3H), 4.89 and 5.55 (q, 2H, AB type, J=14.6 Hz), 6.94–7.23 (m, 7H)

Example 40

2-Ethyl-6,11-dihydrodibenz[b,e]oxepin-11-carboxylic acid (Compound B)

The similar procedures as in Example 39 were repeated except using 23.8 g of 6,11-dihydro-2-ethyldibenz[b,e]oxepin-11-one in place of 6,11-dihydro-2-methyldibenz[b,e]oxepin-11-one to obtain 6.28 g of Compound B.

Melting Point: 154.0°–155.0° C. IR (KBr tablet: cm$^{-1}$): 3072, 2960, 1710, 1699, 1501, 1281 NMR (δ, ppm; CDCl$_3$): 1.19 (t, 3H, J=7.5 Hz), 2.58 (q, 2H, J=7.5 Hz), 4.66 (s, 1H), 4.89 and 5.56 (q, 2H, AB type, J=14.6 Hz), 6.86–7.27 (m, 7H)

Example 41

6,11-Dihydro-2-isopropyldibenz[b,e]oxepin-11-carboxylic acid (Compound C)

The similar procedures as in Example 39 were repeated except using 25.0 g of 6,11-dihydro-2-isopropyldibenz[b,e]oxepin-11-one in place of 6,11-dihydro-2-methyldibenz[b,e]oxepin-11-one to obtain 5.98 g of Compound C.

Melting Point: 161°–162° C. IR (KBr tablet: cm$^{-1}$): 3068, 2948, 1707, 1699, 1499, 1280 NMR (δ, ppm; CDCl$_3$): 1.21 (d, 6H, J=6.8 Hz), 2.78–2.94 (m, 1H), 4.69 (s, 1H), 4.90 and 5.56 (q, 2H, AB type, J=14.5 Hz), 6.88–7.35 (m, 7H)

Example 42

2-(tert-Butyl)-6,11-dihydrodibenz[b,e]oxepin-11-carboxylic acid (Compound D)

The similar procedures as in Example 39 were repeated except using 13.3 g of 2-(tert-butyl)-6,11-dihydrodibenz[b,e]oxepin-11-one in place of 6,11-dihydro-2-methyldibenz[b,e]oxepin-11-one to obtain 3.71 g of Compound D.

Melting Point: 197.0°–198.0° C. IR (KBr tablet: cm$^{-1}$): 3054, 2966, 2870, 1719, 1710, 1501, 1283 NMR (δ, ppm; CDCl$_3$): 1.28 (s, 9H), 4.70 (s, 1H), 4.89 and 5.56 (q, 2H, AB type, J=14.6Hz), 6.87–7.34 (m, 7H)

Example 43

6,11-dihydrodibenz[b,e]oxepin-11-carboxylic acid (Compound E)

The similar procedures as in Example 39 were repeated except using 13.9 g of 6,11-dihydrodibenz[b,e]oxepin-11-one in place of 6,11-dihydro-2-methyldibenz[b,e]oxepin-11one to obtain 7.65 g of Compound E.

Melting Point: 199.5°–201.0° C. IR (KBr tablet: cm$^{-1}$): 3048, 2954, 2888, 1719, 1711, 1703, 1504, 1282 NMR (δ, ppm; CDCl$_3$): 4.67 (s, 1H), 4.85 and 5.57 (q, 2H, AB type, J=14.3 Hz), 6.93–7.24 (m, 8H), 10.38 (brs, 1H)

Example 44

2-Fluoro-6,11-dihydrodibenz[b,e]oxepin-11-carboxylic acid (Compound F)

The similar procedures as in Example 39 were repeated except using 19.0 g of 2-fluoro-6,11-dihydrodibenz[b,e]oxepin-11-one in place of 6,11-dihydro-2-methyldibenz[b,e]oxepin-11-one to obtain 2.17 g of Compound F. Melting Point: 176.0°–177.0° C. IR (KBr tablet: cm$^{-1}$): 3002, 2894, 2666, 1719, 1711, 1694, 1494, 1282 NMR (δ, ppm; CDCl$_3$): 4.59 (s, 1H), 4.88 and 5.52 (q, 2H, AB type, J=14.7 Hz), 6.94 (d, 1H, J=6.6 Hz), 7.0–7.33 (m, 6H), 8.97 (brs, 1H)

Example 45

2-Chloro-6,11-dihydrodibenz[b,e]oxepin-11-carboxylic acid (Compound G)

The similar procedures as in Example 39 were repeated except using 12.2 g of 2-chloro-6,11-dihydrodibenz[b,e]oxepin-11-one in place of 6,11-dihydro-2-methyldibenz[b,e]oxepin-11-one to obtain 7.00 g of Compound G.

Melting Point: 182.0°–183.0° C. IR (KBr tablet: cm$^{-1}$): 3014, 2962, 1713, 1702, 1691, 1485, 1210 NMR (δ, ppm; CDCl$_3$): 4.62 (s, 1H), 4.86 and 5.56 (q, 2H, AB type, J=14.0 Hz), 6.90 (d, 1H, J=8.6 Hz), 6.99–7.36 (m, 6H)

Example 46

2-Bromo-6,11-dihydrodibenz[b,e]oxepin-11-carboxylic acid (Compound H)

The similar procedures as in Example 39 were repeated except using 14.5 g of 2-bromo-6,11-dihydrodibenz[b,e]oxepin-11-one in place of 6,11-dihydro-2-methyldibenz[b,e]oxepin-11-one to obtain 2.00 g of Compound H.

Melting Point: 174.0–175.5 IR (KBr tablet: cm$^{-1}$): 2992, 2902, 1713, 1702, 1690, 1482, 1224 NMR (δ, ppm; CDCl$_3$): 4.62 (s, 1H), 4.86 and 5.56 (q, 2H, AB type, J=14.2 Hz), 6.84 (d, 1H, J=8.6 Hz), 7.13–7.35 (m, 6H), 7.94 (brs, 1H)

Example 47

2-Cyano-6,11-dihydrodibenz[b,e]oxepin-11-carboxylic acid (Compound J)

The similar procedures as in Example 39 were repeated except using 5.10 g of 2-cyano-6,11-dihydrodibenz[b,e]oxepin-11-one in place of 6,11-dihydro-2-methyldibenz[b,e]oxepin-11-one to obtain 1.69 g of Compound J.

Melting Point: 215.0°–217.0° C. IR (KBr tablet: cm$^{-1}$): 3358, 2226, 1726, 1713, 1494, 1254 NMR (δ, ppm; CDCl$_3$): 4.74(s, 1H), 4.89 and 5.68 (q, 2H, AB type, J=13.6 Hz), 6.94 (d, 1H, J=8.3 Hz), 7.09–7.55 (m, 6H)

Example 48

3-Bromo-6,11-dihydrodibenz[b,e]oxepin-11-carboxylic acid (Compound K)

The similar procedures as in Example 39 were repeated except using 28.9 g of 3-bromo-6,11-dihydrodibenz[b,e]oxepin-11-one in place of 6,11-dihydro-2-methyldibenz[b,e]oxepin-11-one to obtain 7.58 g of Compound K.

Melting Point: 217.0°–218.0° C. IR (KBr tablet: cm$^{-1}$): 3022, 2902, 1713, 1707, 1694, 1227 NMR (δ, ppm; CDCl$_3$): 4.67 (s, 1H), 4.84 and 5.68 (q, 2H, AB type, J=13.6 Hz), 7.06–7.48 (m, 7H)

Example 49

6,11-Dihydro-2-methoxycarbonyldibenz[b,e]oxepin-11-carboxylic acid (Compound L)

The similar procedures as in Example 39 were repeated except using 15.7 g of 6,11-dihydro-2-methoxycarbonyldibenz[b,e]oxepin-11-one in place of 6,11-dihydro-2methyldibenz[b,e]oxepin-11-one to obtain 9.20 g of 6,11-dihydro-2-methoxycarbonyldibenz[b,e]oxepin-11-carbaldehyde. In 300 ml of acetone/2-methyl-2-propanol (1:1) was dissolved 9.20 g of the resulting carbaldehyde. To the solution was added 60 ml of neutral phosphate pH standard solution, and 130 ml of 0.5M potassium permanganate aqueous solution was added to the mixture at 0° C. The reaction mixture was stirred for 1.5 hours. After the reaction was completed, 50 ml of saturated sodium sulfite aqueous solution was added to the reaction mixture. The pH was adjusted to 2 with 4N hydrochloric acid and extracted with ethyl acetate. The organic layer was washed with saturated sodium chloride aqueous solution, dried over anhydrous magnesium sulfate and concentrated to dryness under reduced pressure to obtain 9.42 g of Compound L.

Melting Point: 223.0°–224.0° C. IR (KBr tablet: cm$^{-1}$): 3148, 2948, 1737, 1726, 1709, 1689, 1667, 1610, 1579 NMR (δ, ppm; CDCl$_3$): 3.87 (s, 3H), 4.81 (s, 1H), 4.87 and 5.68 (q, 2H, AB type, J=13.6 Hz), 6.92 (d, 1H, J=8.6 Hz), 7.25–7.30 (m, 4H), 7.90 (dd, 1H, J=8.9 and 5.2 Hz), 7.94 (brs, 1H)

Example 50

6,11-Dihydro-2-iododibenz[b,e]oxepin-11-carboxylic acid (Compound M)

In a nitrogen atmosphere, 30.9 g of 6,11-dihydro-2-iododibenz[b,e]oxepin-11-one was dissolved in 100 ml of dichloromethane. After 37.9 ml of cyanotrimethylsilane and 2.9 g of zinc iodide were added to the solution, the mixture was stirred at room temperature for 72 hours. After the reaction was completed, the reaction mixture was diluted with dichloromethane. The diluted solution was washed with saturated sodium bicarbonate aqueous solution and saturated sodium chloride aqueous solution successively, dried over anhydrous magnesium sulfate, and concentrated under reduced pressure to obtain 38.2 g of 6,11-dihydro-2-iodo-11-trimethylsilyloxydibenz[b,e]oxepin-11-carbonitrile.

A mixture of 38.2 g of the compound obtained above, 41.4 g of stannous chloride and 200 ml of hydrochloric acid·acetic acid (1:1) was heated under reflux for 4 hours. The reaction mixture was allowed to stand at room temperature, and 100 ml of water was added. The reaction mixture was extracted with ethyl acetate. The extract was washed with water. The organic layer was extracted 3 times with saturated sodium bicarbonate aqueous solution. The aqueous layer was adjusted to pH 2 with 4N hydrochloric acid, and extracted with ethyl acetate. The organic layer was washed with water and saturated sodium chloride aqueous solution, dried over anhydrous magnesium sulfate and concentrated to dryness under reduced pressure to obtain 8.62 g of Compound M.

Melting Point: 191.0°–192.0° C. IR (KBr tablet: cm$^{-1}$): 3036, 2998, 1711, 1704, 1691, 1478, 1271 NMR ($\delta$, ppm; CDCl$_3$): 4.62 (s, 1H), 4.85 and 5.58 (q, 2H, AB type, J=14.2 Hz), 6.72 (d, 1H, J=8.1 Hz), 7.04–7.71 (m, 6H)

Example 51

6,11-Dihydro-2-trifluoromethyldibenz[b,e]oxepin-11-carboxylic acid (Compound N)

The similar procedures as in Example 50 were repeated except using 19.8 g of 6,11-dihydro-2-trifluoromethyldibenz[b,e]oxepin-11-one in place of 6,11-dihydro-2iododibenz[b,e]oxepin-11-one to obtain 7.78 g of Compoound N.

Melting Point: 258.0°–260.0° C. IR (KBr tablet: cm$^{-1}$): 3070, 2922, 1707, 1693, 1334, 1280 NMR ($\delta$, ppm; CDCl$_3$): 4.78 (s, 1H), 4.87 and 5.76 (q, 2H, AB type, J=13.8 Hz), 6.82–7.95(m, 7H)

Example 52

6,11-Dihydro-2-methoxydibenz[b,e]oxepin-11-carboxylic acid (Compound P)

The similar procedures as in Example 50 were repeated except using 4.80 g of 6,11-dihydro-2-methoxydibenz[b,e]oxepin-11-one in place of 6,11-dihydro-2-iododibenz[b,e]oxepin-11-one to obtain 2.10 g of Compound P. IR (KBr tablet: cm$^{-1}$): 3032, 2912, 1689, 1466, 1225, 1190 NMR ($\delta$, ppm; CDCl$_3$): 3.74 (s, 3H), 4.59 (s, 1H), 4.89 and 5.50 (q, 2H, AB type, J=14.8 Hz), 6.71–7.25 (m, 7H), 9.15 (brs, 1H)

Example 53

4-Bromo-6,11-dihydro-2-methyldibenz[b,e]oxepin-11-carboxylic acid (Compound Q)

The similar procedures as in Example 50 were repeated except using 15.2 g of 4-bromo-6,11-dihydro-2-methyldibenz[b,e]oxepin-11-one in place of 6,11-dihydro-2-iododibenz[b,e]oxepin-11-one to obtain 8.62 g of Compound Q.

Melting Point: 196.0°–197.0° C. IR (KBr tablet: cm$^{-1}$): 3025, 2858, 1712, 1692, 1481, 1216 NMR ($\delta$, ppm; CDCl$_3$): 2.26 (s, 3H), 4.59 (s, 1H), 4.99 and 5.56 (q, 2H, AB type, J=14.7 Hz), 7.05–7.62 (m, 6H)

Example 54

9-Bromo-6,11-dihydrodibenz[b,e]oxepin-11-carboxylic acid (Compound R)

A mixture of 5.48 g of 9-bromo-6,11-dihydrodibenz[b,e]oxepin-11-carbonitrile, 80 ml of conc. hydrochloric acid and 80 ml of acetic acid was heated under reflux for 15 hours. The reaction mixture was allowed to stand at room temperature. The crystals precipitated were collected by filtration and dissolved in dichloromethane. The solution was washed with water, dried and concentrated to dryness under reduced pressure. The crude crystals were recrystallized from toluene to obtain 1.83 g of Compound R.

Melting Point: 187.0°–189.0° C. IR (KBr tablet: cm$^{-1}$): 3410, 1720, 1574, 1486, 1407, 1307, 1211 NMR ($\delta$, ppm; CDCl$_3$): 4.60 (s, 1H), 4.82 and 5.48 (q, 2H, AB type, J=14.6 Hz), 6.85–7.41 (m, 7H), 9.32 (brs, 1H)

Example 55

9-Bromo-6,11-dihydro-2-methyldibenz[b,e]oxepin-11-carboxylic acid (Compound S)

The similar procedures as in Example 54 were repeated except using 6.24 g of 9-bromo-6,11-dihydro-2-methyldibenz[b,e]oxepin-11-carbonitrile in place of 9-bromo6,11-dihydrodibenz[b,e]oxepin-11-carbonitrile to obtain 5.02 g of Compound S.

Melting Point: 168.0°–170.0° C. IR (KBr tablet: cm$^{-1}$): 3420, 1718, 1600, 1505, 1405, 1381, 1251 NMR ($\delta$, ppm; CDCl$_3$): 2.26 (s, 3H), 4.53 (s, 1H), 4.81 and 5.44 (q, 2H, AB type, J=14.7 Hz), 6.80–7.52 (m, 6H), 8.61 (brs, 1H)

Example 56

2,9-Dibromo-6,11-dihydrodibenz[b,e]oxepin-11-carboxylic acid (Compound T)

The similar procedures as in Example 54 were repeated except using 3.85 g of 2,9-dibromo-6,11-dihydrodibenz[b,e]oxepin-11-carbonitrile in place of 9-bromo-6,11dihydrodibenz[b,e]oxepin-11-carbonitrile to obtain 1.77 g of Compound T.

Melting Point: 179.0°–181.5° C. IR (KBr tablet: cm$^{-1}$): 3420, 1720, 1600, 1498, 1385, 1220, 1120 NMR ($\delta$, ppm; CDCl$_3$): 4.54 (s, 1H), 4.81 and 5.47 (q, 2H, AB type, J=14.4 Hz), 6.72–7.58 (m, 6H), 8.56 (brs, 1H)

Example 57

5,11-dihydrobenzoxepino[3,4-b]pyridin-5-carboxylic acid (Compound U)

A mixture of 2.03 g of 5,11-dihydrobenzoxepino[3,4-b]pyridin-5-carbonitrile, 30 ml of hydrochloric acid and 30 ml of acetic acid was heated under reflux for 19 hours. The reaction mixture was allowed to stand at room temperature. Water and dichloromethane were added to the reaction mixture and the pH was adjusted to 3.4 with 10N sodium hydroxide. The organic layer was dried over anhydrous magnesium sulfate, and filtered. The filtrate was concentrated to dryness under reduced pressure to obtain 1.95 g of Compound U.

Melting Point: 139.0°–140.0° C. IR (KBr tablet: cm$^{-1}$): 3450, 1718, 1592, 1496, 1455, 1273 NMR (DMSOd$_6$+ CDCl$_3$): 4.66 (s, 1H), 4.93 and 5.50 (q, 2H, AB type, J=15.8 Hz), 6.97–7.77 (m, 7H), 8.51 (dd, 1H, J=1.5 and 4.8 Hz)

Example 58

5,11-Dihydro-7-methoxybenzoxepino[3,4-b]pyridin-5-carboxylic acid (Compound W)

The similar procedures as in Example 57 were repeated except using 3.10 g of 5,11-dihydro-7-methoxybenzoxepino[3,4-b]pyridin-5-carbonitrile in place of 5,11-dihydrobenzoxepino[3,4-b]pyridin-5-carbonitrile to obtain 2.07 g of Compound W.

Melting Point: 140°–141° C. IR (KBr tablet: cm$^{-1}$): 3430, 1713, 1605, 1497, 1426, 1299 NMR (DMSOd$_6$+CDCl$_3$): 3.75 (s, 3H), 4.64 (s, 1H), 4.86 and 5.37 (q, 2H, AB type, J=16.4 Hz), 6.70–7.23 (m, 5H), 7.63 (dd, 1H, J=3.4 and 4.5 Hz), 8.39 (dd, 1H, J=1.4 and 4.5 Hz)

Example 59

7-Bromo-5,11-dihydrobenzoxepino[3,4-b]pyridin-5-carboxylic acid (Compound X)

The similar procedures as in Example 57 were repeated except using 1.53 g of 7-bromo-5,11-dihydrobenzoxepino[3,4-b]pyridin-5-carbonitrile in place of 5,11dihydrobenzoxepino[3,4-b]pyridin-5-carbonitrile to obtain 1.54 g of Compound X.

Melting Point: 126°–127° C. IR (KBr tablet: cm$^{-1}$): 2940, 1719, 1645, 1590, 1482, 1371 NMR (DMSOd$_6$+CDCl$_3$): 4.83 (s, 1H), 4.91 and 5.47 (q, 2H, AB type, J=15.6 Hz), 6.93–7.75 (m, 6H), 8.42 (dd, 1H, J=1.6 and 4.7 Hz)

Example 60

(−)-2-Bromo-6,11-dihydrodibenz[b,e]oxepin-11-carboxylic acid (Compound Y)

In 500 ml of methanol were dissolved 50.0 g of 2-bromo-6,11-dihydrodibenz[b,e]oxepin-11-carboxylic acid (Compound H) obtained in Example 46 and 46.1 g of (−)-cinchonidine. The solution was stirred at room temperature and then concentrated to dryness under reduced pressure. The obtained crystals were recrystallized from isopropanol 4 times to obtain 32.81 g of (−)-cinchonidine salt of (−) form of Compound H. 16.0 g of the resulting salt was suspended in 200 ml of water and 300 ml of ethyl acetate, and 200 ml of 0.5N hydrochloric acid was added to the suspension under ice cooling. The organic layer was washed with water and saturated sodium chloride aqueous solution, dried over anhydrous magnesium sulfate and concentrated to dryness under reduced pressure to obtain 7.66 g of Compound Y [(−) form of Compound H].

Melting Point: 166.5°–167° C. [α]$_D^{20}$ =−139.0° (c=1.0, CH$_3$OH)

Example 61

(+)-2-Bromo-6,11-dihydrodibenz[b,e]oxepin-11-carboxylic acid (Compound Z)

In 500 ml of methanol were dissolved 50.0 g of 2-bromo-6,11-dihydrodibenz[b,e]oxepin-11-carboxylic acid (Compound H) obtained in Example 46 and 46.1 g of (−)-cinchonidine. The solution was stirred at room temperature and then concentrated to dryness under reduced pressure. The crystals obtained were recrystallized from isopropanol. The mother liquor was concentrated to dryness to obtain 31.5 g of the salt. Using 23.0 g of the resulting salt, recrystallization from isopropnaol-isopropyl ether was repeated 8 times to obtain 0.75 g of (−)-cinchonidine salt of (+) form of Compound H. After 0.75 g of the resulting salt was suspended in 15 ml of water and 30 ml of ethyl acetate, 5 ml of 0.5N hydrochloric acid was added to the suspension under ice cooling. The organic layer was washed with water and saturated sodium chloride aqueous solution, dried over anhydrous magnesium sulfate and concentrated to dryness under reduced pressure to obtain 0.39 g of Compound Z [(+) form of Compound H].

Melting Point: 167.5°–168° C. [α]$_D^{20}$=+143.8° (c=1.0, CH$_3$OH)

Example 62

6,11-Dihydro-2-nitrodibenz[b,e]oxepin-11-carboxylic acid (Compound AA)

The similar procedures as in Example 54 were repeated except using 3.82 g of 6,11-dihydro-2-nitrodibenz[b,e]oxepin-11-carbonitrile in place of 9-bromo-6,11-dihydrodibenz[b,e]oxepin-11-carbonitrile to obtain 1.82 g of Compound AA.

Melting Point: 254°–256° C. IR (KBr tablet: cm$^{-1}$): 3360, 1725, 1715, 1490, 1250 NMR (δ, ppm; CDCl$_3$+DMSO-d$_6$): 4.93 (s, 1H), 4.92 and 5.30 (q, 2H, AB type, J=13.7 Hz), 7.01 (d, 2H, J=9 Hz), 7.06–7.52 (m, 4H), 8.06 (dd, 1H, J=2.8 and 8.9 Hz), 8.22 (d, 1H, J=2.9 Hz)

Example 63

6,11-Dihydro-2,3-dimethyldibenz[b,e]oxepin-11-carboxylic acid (Compound AB)

The similar procedures as in Example 54 were repeated except using 2.0 g of 6,11-dihydro-2,3-dimethyldibenz[b,e]oxepin-11-carbonitrile in place of 9-bromo-6,11dihydrodibenz[b,e]oxepin-11-carbonitrile to obtain 1.71 g of Compound AB.

Melting Point: 195.5°–196.5° C. IR (KBr tablet: cm$^{-1}$): 2900, 1711, 1624, 1508, 1452, 1311 NMR (δ, ppm; CDCl$_3$): 2.16 (s, 6H), 4.63 (s, 1H), 4.83 and 5.54 (q, 2H, AB type, J=14.1 Hz), 6.76 (s, 1H), 6.97 (s, 1H), 7.11–7.28 (m, 4H)

Example 64

6,11-Dihydro-1,4-dimethyldibenz[b,e]oxepin-11-carboxylic acid (Compound AC)

The similar procedures as in Example 54 were repeated using 18.98 g of 6,11-dihydro-1,4-dimethyldibenz[b,e]oxepin-11-carbonitrile in place of 9-bromo-6,11-dihydrodibenz[b,e]oxepin-11-carbonitrile to obtain 7.46 g of Compound AC.

Melting Point: 258°–259° C. IR (KBr tablet: cm$^{-1}$): 2920, 1686, 1493, 1415, 1226 NMR (δ, ppm; CDCl$_3$): 2.25 (s, 3H), 2.37 (s, 3H), 4.74 (s, 1H), 4.91 and 5.47 (q, 2H, AB type, J=15.5 Hz), 6.76–7.71 (m, 6H)

Example 65

6,11-Dihydro-4-methoxycarbonyl-2-methyldibenz[b,e]oxepin-11-carboxylic acid-(Compound AD)

The similar procedures as in Example 49 were repeated except using 13.7 g of 6,11-dihydro-4-methoxycarbonyl-2-methyldibenz[b,e]oxepin-11-one in place of 6,11-dihydro-2-methoxycarbonyldibenz[b,e]oxepin-11-one to obtain 7.70 g of Compound AD Melting Point: 240°–242° C. IR (KBr tablet: cm$^{-1}$): 3150, 2850, 1730, 1690, 1610, 1580 NMR (δ, ppm; CDCl$_3$): 2.25 (s, 3H), 3.68 (s, 3H), 4.54 (s, 1H), 5.02 and 5.53 (q, 2H, AB type, J=14.8 Hz), 6.99–7.29 (m, 6H)

Example 66

2-Bromo-6,11-dihydro-4-nitrodibenz[b,e]oxepin-11-carboxylic acid (Compound AE)

The similar procedures as in Example 54 were repeated except using 20.28 g of 2-bromo-6,11-dihydro-4-nitrodibenz[b,e]oxepin-11-carbonitrile in place of 9-bromo-6,11-dihydrodibenz[b,e]oxepine-11-carbonitrile to obtain 3.36 g of Compound AE.

Melting Point: 203°–205.5° C. (decomposed) IR (KBr tablet: cm$^{-1}$l): 3075, 1715, 1530, 1476, 1303, 1253 NMR (δ, ppm; CDCl$_3$+DMSO-d$_6$): 4.68 (s, 1H), 5.15 and 5.72 (q, 2H, AB type, J=14.5 Hz), 7.10–7.42 (m, 5H), 7.63 (d, 1H, J=2.4 Hz), 7.77 (d, 1H, J=2.4 Hz)

Example 67

2-Bromo-6,11-dihydro-1,3-dimethyldibenz[b,e]oxepin-11-carboxylic acid (Compound AF)

The similar procedures as in Example 54 were repeated except using 14.15 g of 2-bromo-6,11-dihydro-1,3-dimethyldibenz[b,e]oxepin-11-carbonitrile in place of 9-bromo-6,11-dihydrodibenz[b,e]oxepin-11-carbonitrile to obtain 4.91 g of Compound AF.

Melting Point: 221°–224° C. IR (KBr tablet: cm$^{-1}$): 2975, 1683, 1599, 1448, 1269, 1224 NMR (δ, ppm; CDCl$_3$): 2.35 (s, 3H), 2.47 (s, 3H), 4.86 (s, 1H), 4.91 and 5.49 (q, 2H, AB type, J=15.5 Hz), 6.90–7.24 (m, 5H)

Example 68

4-Chloro-6,11-dihydro-1,2-dimethyldibenz[b,e]oxepin-11-carboxylic acid (Compound AG)

The similar procedures as in Example 54 were repeated except using 5.20 g of 4-chloro-6,11-dihydro-1,2-dimethyldibenz[b,e]oxepin-11-carbonitrile in place of 9-bromo-6,11-dihydrodibenz[b,e]oxepin-11-carbonitrile to obtain 3.26 g of Compound AG.

Melting Point: 241°–243° C. (decomposed) IR (KBr tablet: cm$^{-1}$): 2900, 1710, 1692, 1472, 1300, 1229 NMR (δ, ppm; CDCl$_3$+DMSO-d$_6$): 2.21 (s, 3H), 2.29 (s, 3H), 4.84 (s, 1H), 5.03 and 5.51 (q, 2 H, AB type, J=15.6 Hz), 6.89–7.33 (m, 8H)

Example 69

6,11-Dihydro-2-methylthiodibenz[b,e]oxepin-11-carboxylic acid (Compound AH)

The similar procedures as in Example 54 were repeated except using 11.7 g of 6,11-dihydro-2-methylthiodibenz[b,e]oxepin-11-carbonitrile in place of 9-bromo-6,11dihydrodibenz[b,e]oxepin-11-carbonitrile to obtain 2.7 g of Compound AH.

Melting Point: 175°–176° C. IR (KBr tablet: cm$^{-1}$): 2880, 1713, 1695, 1486, 1279, 1245 NMR (δ, ppm; CDCl$_3$): 2.43(s, 3H), 4.64 (s, 1H), 4.86 and 5.56 (q, 2H, type, J=14.4 Hz), 6.87–7.29 (m, 8H)

Example 70

2-Bromo-6,11-dihydro-10-methyldibenz[b,e]oxepin-11-carboxylic acid (Compound AI)

The similar procedures as in Example 54 were repeated except using 4.15 g of 2-bromo-6,11-dihydro-10methyldibenz[b,e]oxepin-11-carbonitrile in place of 9-bromo6,11-dihydrodibenz[b,e]oxepin-11-carbonitrile to obtain 3.54 g of Compound AI.

Melting Point: 185°–187° C. IR (KBr tablet: cm$^-$): 3025, 2900, 1705, 1481, 1240 1205 NMR (δ, ppm; CDCl$_3$): 2.46(s, 3H), 5.04 (s, 1H), 4.80 and 5.57 (q, 2H, AB type, J=13.6 Hz), 6.78 (d, 1H, J=8.1 Hz), 6.99–7.33 (m, 5H)

Example 71

6,11-Dihydro-1,3-dimethyldibenz[b,e]oxepin-11-carboxylic acid (Compound AJ)

The similar procedures as in Example 54 were repeated except using 5.46 g of 6,11-dihydro-1,3-dimethyldibenz[b,e]oxepin-11-carbonitrile in place of 9-bromo-6,11dihydrodibenz[b,e]oxepin-11-carbonitrile to obtain 5.63 g of Compound AJ.

Melting Point: 203°–205° C. IR (KBr tablet: cm$^{-1}$): 2950, 1805, 1681, 1614, 1413, 1228 NMR (δ, ppm; CDCl$_3$): 2.24 (s, 3H), 2.35 (s, 3H), 4.81 (s, 1H), 4.91 and 5.49 (q, 2H, AB type, J=15.4 Hz), 6.75–7.24 (m, 6H)

Example 72

4-Chloro-6,11-dihydro-1-methyldibenz[b,e]oxepin-11-carboxylic acid (Compound AK)

The similar procedures as in Example 54 were repeated except using 5.07 g of 4-chloro-6,11-dihydro-1-methyldibenz[b,e]oxepin-11-carbonitrile in place of 9-bromo6,11- dihydrodibenz[b,e]oxepin-11-carbonitrile to obtain 3.50 g of Compound AK.

Melting Point: 241.5°–243° C. IR (KBr tablet: cm$^{-1}$): 2900, 1693, 1495, 1413, 1274 NMR (δ, ppm; CDCl$_3$): 2.40 (s, 3H), 4.78 (s, 1H), 5.03 and 5.54 (q, 2H, AB type, J=15.6 Hz), 6.83–7.54 (m, 6H)

Example 73

2-Bromo-N-(2,6-dichlorophenyl)-6,11-dihydrodibenz[b,e]oxepin-11-carboxamide (Compound 39)

The similar procedures as in Example 1 were repeated except using 1.67 g of 2-bromo-6,11-dihydrodibenz[b,e] oxepin-11-carboxylic acid obtained in Example 46 (Compound H) in place of Compound A and 0.76 g of 2,6-dichloroaniline in place of aniline to obtain 0.40 g of Compound 39.

Melting Point: 185°–187° C. IR (KBr tablet: cm$^{-1}$): 3225, 3025, 1730, 1658, 1511, 1436, 1231 NMR (δ, ppm; CDCl$_3$): 4.75 (s, 1H), 4.94 and 5.70 (q, 2H, AB type, J=14.2 Hz), 6.88 (d, 1H, J=8.6 Hz), 7.01–7.50 (m, 11H)

Example 74

2-Bromo-N-(2,4-difluorophenyl)-6,11-dihydrodibenz-[b,e]oxepin-11-carboxamide (Compound 40)

The similar procedures as in Example 1 were repeated except using 1.0 g of 2-bromo-6,11-dihydrodibenz[b,e]oxepin-11-carboxylic acid obtained in Example 46 (Compound H) in place of Compound A and 0.48 g of 2,4-difluoroaniline in place of aniline to obtain 0.64 g of Compound 40.

Melting Point: 189°–191° C. IR (KBr tablet: cm$^{-1}$): 3388, 3070, 1611, 1512, 1400, 1302, 1204 NMR (δ, ppm; CDCl$_3$): 4.69 (s, 1H), 4.93 and 5.48 (q, 2H, AB type, J=14.7 Hz), 6.91 (d, 1H, J=8.6 Hz), 6.62–8.28 (m, 11H)

Example 75

5,11-Dihydro-N-(2,6-diisopropylphenyl)-7-methoxybenzoxepino[3,4-b]pyridin-5-carboxamide (Compound 41)

The similar procedures as in Example 1 were repeated except using 0.74 g of 5,11-dihydro-7-methoxybenzoxepino[3,4-b]pyridin-5-carboxylic acid obtained in Example 58 (Compound W) in place of Compound A and 0.72 g of 2,6-diisopropylaniline in place of aniline to obtain 0.86 g of Compound 41.

Melting Point: 180.5°–181° C. IR (KBr tablet: cm$^{-1}$): 3160, 2950, 1690, 1586, 1511, 1300 NMR (δ, ppm; CDCl$_3$): 0.98 (d, 12H, J=6.8 Hz), 2.54–2.78 (m, 2H), 3.80 (s, 3H), 4.81 (s, 1H), 5.11 and 5.51 (q, 2H, AB type, J=16.3 Hz), 6.81–7.30 (m, 7H), 7.83 (dd, 1H, J=1.3 and 7.9 Hz), 8.02 (brs, 1H), 8.50 (dd, 1H, J=1.3 and 4.7 Hz)

Example 76

2-Bromo-5,11-dihydro-N-(2,6-diisopropylphenyl)-benzoxepino[3,4-b]pyridin-5-carboxamide (Compound 42)

The similar procedures as in Example 1 were repeated except using 1.40 g of 7-bromo-5,11-dihydrobenzoxepino[3,4-b]pyridin-5-carboxylic acid obtained in Example 59 (Compound X) in place of Compound A and 1.16 g of 2,6-diisopropylaniline in place of aniline to obtain 1.79 g of Compound 42.

Melting Point: 151°–153° C. IR (KBr tablet: cm$^{-1}$): 3268, 2962, 1640, 1584, 1485, 1224 NMR (δ, ppm; CDCl$_3$): 0.99 (d, 6H, J=7.0 Hz), 1.01 (d, 6H, J=7.0 Hz), 2.63–2.83 (m, 2H), 4.78 (s, 1H), 5.11 and 5.57 (q, 2H, AB type, J=16.2 Hz), 7.0–7.62 (m, 8H), 7.83 (dd, 1H, J=1.3 and 7.9 Hz), 8.52 (dd, 1H, J=1.3 and 4.6 Hz)

Example 77

2-Bromo-6,11-dihydro-N-phenyl-N-methyldibenz-[b,e]oxepin-11-carboxamide (Compound 43)

The similar procedures as in Example 1 were repeated except using 1.0 g of 2-bromo-6,11-dihydrodibenz[b,e]oxepin-11-carboxylic acid obtained in Example 46 (Compound H) in place of Compound A and 0.41 g of N-methylaniline in place of aniline to obtain 0.63 g of Compound 43.

Melting Point: 148°–148.5° C. IR (KBr tablet: cm$^{-1}$): 3056, 2896, 1660, 1596, 1480, 1382, 1236 NMR (δ, ppm; CDCl$_3$): 3.26 (s, 3H), 4.78 (s, 1H), 4.78 and 6.11 (q, 2H, AB type, J=13.6 Hz), 6.58–7.42 (m, 12H)

EXAMPLE 78

2-Bromo-6,11-dihydro-N-(2,6-diisopropyl-4-methyl-thiophenyl)dibenz[b,e]oxepin-11-carboxamide (Compound 44)

The similar procedures as in Example 1 were repeated except using 1.0 g of 2-bromo-6,11-dihydrodibenz[b,e]oxepin-11-carboxylic acid obtained in Example 46 (Compound H) in place of Compound A and 0.84 g of 2,6-diisopropyl-4-methylthioaniline in place of aniline to obtain 1.25 g of Compound 44.

Melting Point: 171°–172° C. IR (KBr tablet: cm$^{-1}$): 3266, 2960, 1650, 1526, 1481, 1233 NMR (δ, ppm; CDCl$_3$): 0.99 (d, 6H, J=6.8 Hz), 1.02 (d, 6H, J=6.8 Hz), 2.43 (s, 3H), 2.55–2.86 (m, 2H), 4.81 (s, 1H), 5.01 and 5.54 (q, 2H, AB type, J=14.6 Hz), 6.93–7.55 (m, 10H)

Example 79

2-(tert-Butyl)-6,11-dihydro-N-(2,6-dichlorophenyl)-dibenz[b,e]oxepin-11-carboxamide (Compound 45)

The similar procedures as in Example 1 were repeated except using 1.0 g of 2-(tert-butyl)-6,11-dihydrodibenz[b,e]oxepine-11-carboxylic acid obtained in Example 42 (Compound D) in place of Compound A and 0.49 g of 2,6-dichloroaniline in place of aniline to obtain 0.92 g of Compound 45.

Melting Point: 115°–117° C. IR (KBr tablet: cm$^{-1}$): 3380, 3248, 2954, 1658, 1480, 1231 NMR (δ, ppm; CDCl$_3$): 1.32 (s, 9H), 4.84 (s, 1H), 4.95 and 5.72 (q, 2H, AB type, J=14.2 Hz), 6.90–7.60 (m, 11H)

Example 80

6,11-Dihydro-N-(2,6-diisopropylphenyl)-2-nitro-dibenz[b,e]-oxepin-11-carboxamide (Compound 46)

The similar procedures as in Example 1 were repeated except using 1.18 g of 6,11-dihydro-2-nitrodibenz[b,e]oxepin-11-carboxylic acid obtained in Example 62 (Compound AA) in place of Compound A and 0.73 g of 2,6-diisopropylaniline in place of aniline to obtain 0.83 g of Compound 46.

Melting Point: 186.5°–187.5° C. IR (KBr tablet: cm$^{-1}$): 3306, 2966, 1658, 1527, 1461, 1236 NMR (δ, ppm; CDCl$_3$): 1.06 (d, 6H, J=6.8 Hz), 1.09 (d, 6H, J=6.8 Hz), 2.63–2.93 (m, 2H), 4.94 (s, 1H), 4.97 and 5.87 (q, 2H, AB type, J=13.5 Hz), 6.75–8.28 (m, 11H)

Example 81

6,11-Dihydro-N-(2,6-diisopropylphenyl)-2-dimethyl-aminocarbonyldibenz[b,e]oxepin-11-carboxamide (Compound 47)

The similar procedures as in Example 1 were repeated except using 0.92 g of 2-carboxy-6,11-dihydro-N-(2,6-diisopropylphenyl)dibenz[b,e]oxepin-11-carboxamide (Compound 25) obtained in Example 25 in place of Compound A and 0.34 g of dimethylamine hydrochloride in place of aniline to obtain 0.70 g of Compound 47.

Melting Point: 200°–203° C. IR (KBr tablet: cm$^{-1}$): 3256, 2960, 2928, 1687, 1621, 1489, 1257 NMR (δ, ppm; CDCl$_3$): 1.0 (d, 6H, J=6.8 Hz), 1.04 (d, 6H, J=6.8 Hz, 2.60–2.90(m, 2H), 3.05 (s, 6H), 4.93 (s, 1H), 5.01 and 5.64 (q, 2H, AB type, J=13.6 Hz), 7.0–7.56 (m, 11H)

Example 82

6,11-Dihydro-N-(2,6-diisorpopylphenyl)-2,3-dimethyldibenz[b,e]oxepin-11-carboxamide (Compound 48)

The similar procedures as in Example 1 were repeated except using 0.84 g of 6,11-dihydro-2,3-dimethyldibenz[b,e]oxepin-11-carboxylic acid obtained in Example 63 (Compound AB) in place of Compound A and 0.83 g of 2,6-diisopropylaniline in place of aniline to obtain 1.25 g of Compound 48.

Melting Point: 164°–165° C. IR (KBr tablet: cm$^{-1}$): 3288, 2960, 1650, 1623, 1497, 1316 NMR (δ, ppm; CDCl$_3$): 0.97 (d, 6H, J=6.8 Hz), 1.01 (d, 6H, J=6.8 Hz), 2.22 (s, 6H), 2.50–2.83 (m, 2H), 4.83 (s, 1H), 5.01 and 5.49 (q, 2H, AB type, J=14.5 Hz), 6.89–7.56 (m, 10H)

Example 83

6,11-Dihydro-N-(2,6-diisopropylphenyl)-1,4-dimethyldibenz[b,e]oxepin-11-carboxamide (Compound 49)

The similar procedures as in Example 1 were repeated except using 1.34 g of 6,11-dihydro-1,4-dimethyldibenz[b,e]oxepin-11-carboxylic acid obtained in Example 64 (Compound AC) in place of Compound A and 1.18 g of 2,6-diisopropylaniline in place of aniline to obtain 1.19 g of Compound 49.

Melting Point: 149°–149.5° C. IR (KBr tablet: cm$^{-1}$): 3308, 2924, 1668, 1512, 1464, 1203 NMR (δ, ppm; CDCl$_3$): 0.95 (d, 6H, J=6.8 Hz), 1.06 (d, 6H, J=6.8 Hz), 2.31 (s, 3H), 2.49 (s, 3H), 2.70–2.93 (m, 2H), 5.16 (s, 1H), 5.02 and 5.47 (q, 2H, AB type, J=15.2 Hz), 6.86–7.58 (m, 10H)

Example 84

6,11-Dihydro-N-(2,6-diethylphenyl)-1,4-dimethyldibenz[b,e]oxepin-11-carboxamide (Compound 50)

The similar procedures as in Example 1 were repeated except using 1.0 g of 6,11-dihydro-1,4-dimethyldibenz[b,e]oxepin-11-carboxylic acid obtained in Example 64 (Compound AC) in place of Compound A and 0.62 g of 2,6-diethylaniline in place of aniline to obtain 0.61 g of Compound 50.

Melting Point: 104°–105.5° C. IR (KBr tablet: cm$^{-1}$): 3380, 2926, 1680, 1468, 1474, 1200 NMR (δ, ppm; CDCl$_3$): 0.96 (t, 6H, J=7.6 Hz), 2.41 (q, 4H, J=7.6 Hz), 2.31 (s, 3H), 2.49 (s, 3H), 5.13 (s, 1H), 5.01 and 5.48 (q, 2H, AB type, J=15.4 Hz), 6.86–7.56 (m, 10H)

Example 85

Methyl 6,11-dihydro-11-(2,6-diisopropylphenyl)aminocarbonyl-2-methyldibenz[b,e]oxepin-4-carboxylate (Compound 51)

The similar procedures as in Example 1 were repeated except using 6.73 g of 6,11-dihydro-4-methoxycarbonyl-2-methyldibenz[b,e]oxepin-11-carboxylic acid obtained in Example 65 (Compound AD) in place of Compound A and 3.82 g of 2,6-diisopropylaniline in place of aniline to obtain 0.86 g of Compound 51.

Melting Point: 135.5°–137.5° C. IR (KBr tablet: cm$^{-1}$): 3280, 2958, 1739, 1653, 1434, 1203 NMR (δ, ppm; CDCl$_3$): 0.93 (d, 6H, J=6.8 Hz), 0.99 (d, 6H, J=6.8 Hz), 2.35 (s, 3H), 2.38–2.79 (m, 2H), 3.93 (s, 3H), 4.89 (s, 1H), 5.25 and 5.50 (q, 2H, AB type, J=15.3 Hz), 6.97–7.67 (m, 10H)

Example 86

6,11-Dihydro-11-(2,6-diisopropylphenyl)aminocarbonyl-2-methyldibenz[b,e]oxepin-4-carboxylic acid (Compound 52)

The similar procedures as in Example 25 were repeated except using 0.43 g of methyl 6,11-dihydro-11-(2,6-diisopropylphenyl)aminocarbonyl-2-methyldibenz[b,e]oxepin-4-carboxylate (Compound 51) obtained in Example 85 in place of Compound 24 to obtain 0.25 g of Compound 52.

Melting Point: 172°–172.5° C. IR (KBr tablet: cm$^{-1}$): 3280, 2868, 1645, 1511, 1446, 1218 NMR (δ, ppm; CDCl$_3$): 1.01(d, 6H, J=6.8 Hz), 1.06 (d, 6H, J=6.8 Hz), 2.37 (s, 3H), 2.63–2.85 (m, 2H), 4.95 (s, 1H), 5.22 and 5.74 (q, 2H, AB type, J=14.8 Hz), 7.01–7.91 (m, 10H)

Example 87

2-Bromo-6,11-dihydro-N-(2,6-diisopropylphenyl)-4-nitrodibenz[b,e]oxepin-11-carboxamide (Compound 53)

The similar procedures as in Example 1 were repeated except using 3.28 g of 2-bromo-6,11-dihydro-4-nitrodibenz[b,e]oxepin-11-carboxylic acid (Compound AE) obtained in Example 66 in place of Compound A and 2.30 g of 2,6-diisopropylaniline in place of aniline to obtain 2.34 g of Compound 53.

Melting Point: 158°–160° C. IR (KBr tablet: cm$^{-1}$): 3282, 2962, 1652, 1544, 1467, 1350 NMR (δ, ppm; CDCl$_3$): 1.05 (d, 6H, J=6.8 Hz), 1.07 (d, 6H, J=6.8 Hz), 2.67–2.90 (m, 2H), 4.86 (s, 1H), 5.30 and 5.67 (q, 2H, AB type, J=15.5 Hz), 6.87 (brs, 1H), 7.06–7.49 (m, 8H), 7.81 (dd, 1H, J=1.8 and 9.9 Hz)

Example 88

2-Bromo-6,11-dihydro-N-(2,6-diisopropylphenyl)-4-aminodibenz[b,e]oxepin-11-carboxamide (Compound 54)

A mixture of 2.28 g of 2-bromo-6,11-dihydro-N(2,6-diisopropylphenyl)-4-nitrodibenz[b,e]oxepin-11-carboxamide (Compound 53) obtained in Example 87, 2.28 g of iron powder, 70 mg of ferric chloride, 10 ml of water and 100 ml of ethanol was heated under reflux for 30 minutes. The reaction mixture was allowed to stand at room temperature and concentrated under reduced pressure. Thereafter ethyl acetate and water were added to the residue and the mixture was rendered alkaline with 10N sodium hydroxide. After the reaction solution was filtered, the organic layer was washed with water and saturated sodium chloride aqueous solution successively. The organic layer was dried and concentrated to dryness under reduced pressure to obtain 2.14 g of Compound 54.

Melting Point: 246°–248.5° C. (decomposed) IR (KBr tablet: cm$^{-1}$): 3482, 3316, 2958, 1668, 1616, 1500, 1220

NMR (δ, ppm; CDCl$_3$): 1.02 (d, 6H, J=6.8 Hz), 1.05 (d, 6H, J=6.8 Hz), 2.56–2.90 (m, 2H), 4.08 (brs,2H), 4.74 (s, 1H), 5.04 and 5.52 (q, 2H, AB type, J=14.6 Hz), 6.82–7.49 (m, 10H)

Example 89

2-Bromo-6,11-dihydro-N-(2,6-diisopropylphenyl)-4-dimethylaminodibenz[b,e]oxepin-11-carboxamide hydrochloride (Compound 55)

After 2.12 g of 2-bromo-6,11-dihydro-N-(2,6-diisopropylphenyl)-4-aminodibenz[b,e]oxepin-11-carboxamide (Compound 54) obtained in Example 88 was dissolved in 80 ml of methanol, 1.35 g of sodium cyanoborohydride and a small amount of Bromocresol Green were added to the solution, and 5.8M hydrochloric acid-ethanol solution were added to the solution under ice cooling to render the solution yellow. While 1.74 g of 37% formalin was added dropwise to the mixture at room temperature, 5.8M hydrochloric acid-ethanol solution was added to keep the reaction solution yellow. After the reaction was completed, the reaction solution was concentrated under reduced pressure and ethyl acetate and water were added to the residue. The mixture was made alkaline with 10N sodium hydroxide. The organic layer was washed with water and saturated sodium chloride aqueous solution successively, dried over anhydrous magnesium sulfate and concentrated under reduced pressure. The resulting residue was purified by silica gel chromatography (hexane: ethyl acetate=5:1) to obtain 1.85 g of 2-bromo-6,11-dihydro-N-(2,6-diisopropylphenyl)-4-dimethylaminodibenz[b,e]oxepin-11-carboxamide.

NMR (δ, ppm; $CDCl_3$): 1.02 (d, 6H, J=6.8 Hz), 1.07 (d, 6H, J=6.8 Hz), 2.63–3.05 (m, 2H), 2.89 (s, 6H), 4.72 (s, 1H), 5.02 and 5.45 (q, 2H, AB type, J=17.5 Hz), 6.96–7.41 (m, 10H)

After the carboxamide obtained was dissolved in 30 ml of isopropanol, 2 ml of 5.4M hydrochloric acid ethanol solution was added to the solution and the mixture was concentrated under reduced pressure. The resulting crude crystals were recrystallized from isopropanol/isopropylether to obtain 1.16 g of Compound 55.

Melting Point: 205.5°–207.5° C. IR (KBr tablet: $cm^{-1}$): 2962, 1682, 1661, 1512, 1493, 1255

Example 90

2-Bromo-6,11-dihydro-N-(2,6-diisopropylphenyl)-1,3-dimethyldibenz[b,e]oxepin-11-carboxamide (Compound 56)

The similar procedures as in Example 1 were repeated except using 3.18 g of 2-bromo-6,11-dihydro-1,3-dimethyldibenz[b,e]oxepin-11-carboxylic acid (Compound AF) obtained in Example 67 in place of Compound A and 1.95 g of 2,6-diisopropylaniline in place of aniline to obtain 1.32 g of Compound 56.

Melting Point: 143.5°–144° C. IR (KBr tablet: $cm^{-1}$): 3294, 2960, 1683, 1659, 1496, 1308 NMR (δ, ppm; $CDCl_3$): 1.02 (d, 6H, J=6.8 Hz), 1.07 (d, 6H, J=6.8 Hz), 2.40 (s, 3H), 2.67 (s, 3H), 2.67–3.04 (m, 2H), 5.18 (s, 1H), 5.02 and 5.49 (q, 2H, AB type, J=15.4 Hz), 6.85–7.55 (m, 9H)

Example 91

2-Bromo-N-(2,6-diethylphenyl)-6,11-dihydro-1,3-dimethyldibenz[b,e]oxepin-11-carboxamide (Compound 57)

The similar procedures as in Example 1 were repeated except using 1.59 g of 2-bromo-6,11-dihydro-1,3-dimethyldibenz[b,e]oxepin-11-carboxylic acid (Compound AF) obtained in Example 67 in place of Compound A and 0.82 g of 2,6-diethylaniline in place of aniline to obtain 0.87 g of Compound 57.

Melting Point: 119.5°–120.5° C. IR (KBr tablet: $cm^{-1}$): 3298, 2962, 1658, 1593, 1441, 1308 NMR (δ, ppm; $CDCl_3$): 1.01 (t, 6H, J=7.5 Hz), 2.44 (q, 4H, J=7.5 Hz), 2.40 (s, 3H), 2.67 (s, 3H), 5.17 (s, 1H), 5.02 and 5.51 (q, 2H, AB type, J=15.4 Hz), 6.94–7.53 (m, 9H)

Example 92

2-Bromo-6,11-dihydro-1,3-dimethyl-N-(2,6-dimethylphenyl)dibenz[b,e]oxepin-11-carboxamide (Compound 58)

The similar procedures as in Example 1 were repeated except using 1.0 g of 2-bromo-6,11-dihydro-1,3-dimethyldibenz[b,e]oxepin-11-carboxylic acid (Compound AF) obtained in Example 67 in place of Compound A and 0.38 g of 2,6-dimethylaniline in place of aniline to obtain 0.55 g of Compound 58.

Melting Point: 214.5°–217.5° C. IR (KBr tablet: $cm^{-1}$): 3376, 2918, 1679, 1599, 1486, 1307 NMR (δ, ppm; $CDCl_3$): 2.10 (s, 6H), 2.39 (s, 3H), 2.66 (s, 3H), 5.14 (s, 1H), 5.01 and 5.53 (q, 2H, AB type, J=15.3 Hz), 6.43–7.56 (m, 9H)

Example 93

4-Chloro-6,11-dihydro-N-(2,6-diisopropylphenyl)-1,2-dimethyldibenz[b,e]oxepin-11-carboxamide (Compound 59)

The similar procedures as in Example 1 were repeated except using 1.60 g of 4-chloro-6,11-dihydro-1,2-dimethyldibenz[b,e]oxepin-11-carboxylic acid (Compound AG) obtained in Example 68 in place of Compound A and 1.36 g of 2,6-diisopropylaniline in place of aniline to obtain 1.85 g of Compound 59.

Melting Point: 110.5°–112° C. IR (KBr tablet: $cm^{-1}$): 3276, 2958, 1680, 1497, 1470, 1219 NMR (δ, ppm; $CDCl_3$): 1.02 (d, 6H, J=7.3 Hz), 1.10 (d, 6H, J=7.3 Hz), 2.25 (s, 3H), 2.40 (s, 3H), 2.67–3.01 (m, 2H), 5.19 (s, 1H), 5.08 and 5.50 (q, 2H, AB type, J=15.6 Hz), 6.99–7.48 (m, 9H)

Example 94

(–)-2-Bromo-6,11-dihydro-N-(2,6-diisopropylphenyl)-dibenz[b,e]oxepin-11-carboxamide (Compound 60)

The similar procedures as in Example 1 were repeated except using 7.38 g of (–)-2-bromo-6,11-dihydrodibenz[b,e]-oxepin-11-carboxylic acid (Compound Y) obtained in Example 60 in place of Compound A and 4.50 g of 2,6-diisopropylaniline in place of aniline to obtain 8.69 g of Compound 60 [(–) form of Compound 18].

Melting Point: 158°–159° C. $[\alpha]_D^{20}$=–94.15° (c=0.8, $CH_3OH$)

Example 95

(+)-2-Bromo-6,11-dihydro-N-(2,6-diisopropylphenyl)-dibenz[b,e]oxepin-11-carboxamide (Compound 61)

The similar procedures as in Example 1 were repeated except using 0.37 g of (+)-2-bromo-6,11-dihydrodibenz[b,e]oxepin-11-carboxylic acid (Compound Z) obtained in Example 61 in place of Compound A and 0.23 g of 2,6-diisopropylaniline in place of aniline to obtain 0.31 g of Compound 61 [(+) form of Compound 18].

Melting Point: 158°–159° C. $[\alpha]_D^{20}$=–92.35° (c=0.8, CH$_3$OH)

Example 96

6,11-Dihydro-N-(2,6-diisopropylphenyl)-1,3-dimethyl-dibenz[b,e]oxepin-11-carboxamide (Compound 62)

The similar procedures as in Example 1 were repeated except using 1.0 g of 6,11-dihydro-1,3-dimethyldibenz[b,e]oxepin-11-carboxylic acid (Compound AJ) obtained in Example 71 in place of Compound A and 0.88 g of 2,6-diisopropylaniline in place of aniline to obtain 0.39 g of Compound 62.

Melting Point: 109.5°–110° C. IR (KBr tablet: cm$^{-1}$): 3316, 2958, 1652, 1511, 1305, 1069 NMR (δ, ppm; CDCl$_3$): 0.96 (d, 6H, J=6.8 Hz), 1.03 (d, 6H, J=6.8 Hz), 2.29 (s, 3H), 2.49 (s, 3H), 2.64–2.95 (m, 2H), 5.17 (s, 1H), 5.04 and 5.46 (q, 2H, AB type, J=15.1 Hz), 6.84–7.59 (m, 10H)

Example 97

6,11-Dihydro-N-(2,6-diethylphenyl)-1,3-dimethyl-dibenz[b,e]oxepin-11-carboxamide (Compound 63)

The similar procedures as in Example 1 were repeated except using 1.0 g of 6,11-dihydro-1,3-dimethyldibenz[b,e]-oxepin-11-carboxylic acid (Compound AJ) obtained in Example 71 in place of Compound A and 0.61 g of 2,6-diethylaniline in place of aniline to obtain 0.53 g of Compound 63.

Melting Point: 108°–109.5° C. IR (KBr tablet: cm$^{-1}$): 3270, 2960, 1658, 1651, 1513, 1305 NMR (δ, ppm; CDCl$_3$): 0.95(t, 6H, J=7.5 Hz), 2.29 (s, 3H), 2.38 (q, 4H, J=7.5 Hz), 2.49 (s, 3H), 5.15 (s, 1H), 5.04 and 5.48 (q, 2H, AB type, J=15.2 Hz), 6.84–7.57 (m, 10H)

Example 98

4-Chloro-6,11-dihydro-N-(2,6-diisopropylphenyl)-1-methyldibenz[b,e]oxepin-11-carboxamide (Compound 64)

The similar procedures as in Example 1 were repeated except using 1.44 g of 4-chloro-6,11-dihydro-1-methyldibenz[b,e]oxepin-11-carboxylic acid (Compound AK) obtained in Example 72 in place of Compound A and 1.25 g of 2,6-diisopropylaniline in place of aniline to obtain 1.39 g of Compound 64.

Melting Point: 114°–116° C. IR (KBr tablet: cm$^{-1}$): 3308, 2958, 1652, 1517, 1446, 1291 NMR (δ, ppm; CDC$_3$): 0.99 (d, 6H, J=8.8 Hz), 1.07 (d, 6H, J=8.8 Hz), 2.51 (s, 3H), 2.70–2.93 (m, 2H), 5.15 (s, 1H), 5.10–5.53 (q, 2H, AB type, J=15.5 Hz), 6.90–7.57 (m, 10H)

Example 99

6,11-Dihydro-N-(2,6-diisopropylphenyl)-2-methyl-thiodibenz[b,e]oxepin-11-carboxamide (Compound 65)

The similar procedures as in Example 1 were repeated except using 1.50 g of 6,11-dihydro-2-methylthiodibenz[b,e]oxepin-11-carboxylic acid (Compound AH) obtained in Example 69 in place of Compound A and 1.12 g of 2,6-diisopropylaniline in place of aniline to obtain 1.43 g of Compound 65.

Melting Point: 171.5°–172.5° C. IR (KBr tablet: cm$^{-1}$): 3288, 2958, 1658, 1652, 1517 1487, 1235 NMR (δ, ppm; CDCl$_3$): 0.98 (d, 6H, J=6.8 Hz), 1.02 (d, 6H, J=6.8 Hz), 2.47 (s, 3H), 2.56–2.83 (m, 2H), 5.03 and 5.52 (q, 2H, AB type, J=13.6 Hz), 6.99–7.52 (m, 11H)

Example 100

2-Bromo-6,11-dihydro-N-(2,6-diethylphenyl)-10-methyldibenz[b,e]oxepin-11-carboxamide (Compound 66)

The similar procedures as in Example 1 were repeated except using 1.0 g of 2-bromo-6,11-dihydro-10-methyldibenz[b,e]oxepin-11-carboxylic acid (Compound AI) obtained in Example 70 in place of Compound A and 0.54 g of 2,6-diethyl aniline in place of aniline to obtain 0.45 g of Compound 66.

Melting Point: 143°–144° C. IR (KBr tablet: cm$^{-1}$): 3250, 2908, 1718, 1680, 1514, 1246 NMR (δ, ppm; CDCl$_3$): 1.05 (t, 6H, J=7.5 Hz), 2.45 (q, 4H, J=7.5 Hz), 2.58 (s, 3H), 5.08 (s, 1H), 4.94 and 5.61 (q, 2H, AB type, J=14.0 Hz), 6.83–7.52 (m, 10H)

Example 101

10,11-Dihydro-N-(2,6-diisopropylphenyl)-5H-dibenzo[a,d]cyclohepten-5-carboxamide (Compound 67)

The similar procedures as in Example 1 were repeated except using 2.03 g of 10,11-dihydro-5H-dibenzo[a,d]cyclohepten-5-carboxylic acid obtained in Reference Example 3 in place of Compound A and 1.81 g of 2,6-diisopropylaniline in place of aniline to obtain 0.72 g of Compound 67.

Melting Point: 140°–142° C. (decomposed) IR (KBr tablet: cm$^{-1}$): 3240, 2864, 1636, 1515, 1444, 1416, 1363, 1225 NMR (δ, ppm; CDCl$_3$): 1.11 (d, 12H, J=7.0 Hz), 2.79–3.14 (m, 4H), 3.32–3.67 (m, 2H), 4.86 (s, 1H), 6.64 (brs, 1H), 7.01–7.47 (m, 11H)

Example 102

10,11-Dihydro-N-(2,6-diisopropylphenyl)-3-methyl-5H-dibenzo[a,d]cyclohepten-5-carboxamide (Compound 68)

The similar procedures as in Example 1 were repeated except using 1.14 g of 10,11-dihydro-3-methyl-5H-dibenzo[a,d]cyclohepten-5-carboxylic acid obtained in Reference Example 4 in place of Compound A and 0.8 g of 2,6-diisopropylaniline in place of aniline to obtain 0.28 g of Compound 68.

Melting Point: 118°–120° C. IR (KBr tablet: cm$^{-1}$): 3300, 2922, 1647, 1512, 1362, 1256 NMR (δ, ppm; CDCl$_3$): 1.11(d, 12H, J=6.8 Hz), 2.32 (s, 3H), 2.81–3.11 (m, 4H), 3.33–3.50 (m, 2H), 4.81 (s, 1H), 6.68(brs,1H), 7.02–7.41 (m, 10H)

Example 103

2-Bromo-10,11-dihydro-N-(2,6-diisopropylphenyl)-5H-dibenzo[a,d]cyclohepten-5-carboxamide (Compound 69)

The similar procedures as in Example 1 were repeated except using 1.20 g of 2-bromo-10,11-dihydro-5H-dibenzo[a,d]cyclohepten-5-carboxylic acid obtained in Reference Example 5 in place of Compound A and 0.81 g of 2,6-diisopropylaniline in place of aniline to obtain 1.70 g of Compound 69.

Melting Point: 127°–128° C. IR (KBr tablet: cm$^{-1}$): 3276, 2864, 1646, 1513, 1487, 1322 NMR (δ, ppm; CDCl$_3$): 1.10 (d, 6H, J=6.8 Hz), 1.13 (d, 6H, J=6.8 Hz), 2.77–3.06 (m, 4H), 3.31–3.50 (m, 2H), 4.79(s, 1H), 6.62 (brs,1H), 6.62–7.51 (m, 10H)

Example 104

N-(2,6-Diisopropylphenyl)-5H-dibenzo[a,d]cyclohepten-5-carboxamide (Compound 70)

The similar procedures as in Example 1 were repeated except using 1.99 g of 5H-dibenzo[a,d]cyclohepten-5-carboxylic acid obtained in Reference Example 6 in place of Compound A and 1.80 g of 2,6-diisopropylaniline in place of aniline to obtain 1.42 g of Compound 70.

Melting Point: 166°–166.5° C. IR (KBr tablet: cm$^{-1}$): 3398, 2852, 1662, 1593, 1443, 1360, 1207 NMR (δ, ppm; CDCl$_3$): 1.07 (d, 12H, J=6.8 Hz), 2.75–3.06 (m, 2H), 5.02 (s, 1H), 6.26 (brs,1H), 7.05 (d, 2H, J=4.6 Hz), 7.12–7.65 (m, 11H)

Example 105

2-Bromo-5,11-dihydro-N-(2,6-diisopropylphenyl)-5-methyl-6-oxo-11H-dibenz[b,e]azepine-11-carboxamide (Compound 71)

The similar procedures as in Example 1 were repeated except using 1.38 g of 2-bromo-5,11-dihydro-5-methyl-6-oxo-11H-dibenz[b,e]azepin-11-carboxylic acid obtained in Reference Example 2 in place of Compound A and 0.86 g of 2,6-diisopropylaniline in place of aniline to obtain 1.60 g of Compound 71.

Melting Point: 241°–243.5° C. (decomposed) IR (KBr tablet: cm$^{-1}$): 3412, 2960, 1623, 1455, 1362 NMR (δ, ppm; CDCl$_3$): 1.10 (d, 6H, J=6.8 Hz), 1.16 (d, 6H, J=6.8 Hz), 2.78–2.94 (m, 2H), 3.53 (s, 3H), 4.74 (s, 1H), 6.46 (brs,1H), 7.02–8.09 (m, 10H)

Reference Example 1

2-Bromo-6,11-dihydrodibenzo[b,e]thiepin-11-carboxylic acid

After 4.72 g of 2-bromo-11-cyano-6,11-dihydrodibenzo[b,e]thiepine was dissolved in 90 ml of hydrochloric acid-acetic acid (1:2), the mixture was heated under reflux for 48 hours. The reaction mixture was allowed to stand at room temperature, and 50 ml of water was added to the reaction mixture, and extracted with ethyl acetate. The extract was washed with water. The organic layer was extracted 3 times with saturated sodium bicarbonate aqueous solution. The aqueous layer was adjusted to pH 2 with 4N hydrochloric acid, and extracted with ethyl acetate. The extract was washed with water and saturated sodium chloride aqueous solution successively, dried over anhydrous magnesium sulfate and concentrated to dryness under reduced pressure to obtain 2.68 g of 2-bromo-6,11-dihydrodibenzo[b,e]thiepin-11-carboxylic acid.

Melting Point: 185.0°–186.0° C. IR (KBr tablet: cm$^{-1}$): 3450, 3020, 2650, 1715, 1700, 1465, 1275, 1210 NMR (δ, ppm; CDCl$_3$): 3.70 and 4.64 (q, 2H, AB type, J=14.8 Hz), 4.77 (s, 1H), 6.99 (d, 1H, J=4.8 Hz), 7.05–7.43 (m, 6H)

Reference Example 2

2-Bromo-5,11-dihydro-5-methyl-6-oxo-11H-dibenz[b,e]azepin-11-carboxylic acid

The similar procedures as in Example 39 were repeated except using 13.3 g of 2-bromo-5,11-dihydro-5-methyl-11H-dibenz[b,e]azepin-6,11-dione in place of 6,11-dihydro-2-methyldibenz[b,e]oxepin-11-one to obtain 5.08 g of 2-bromo-5,11-dihydro-5-methyl-6-oxo-11H-dibenz[b,e]azepin-11-carboxylic acid.

Melting Point: 240.5° C. IR (KBr tablet: cm$^{-1}$): 2895, 1724, 1599, 1562, 1486, 1378, 1194 NMR (δ, ppm; CDCl$_3$): 3.46(s, 3H), 4.76(s, 1H), 7.11–7.85 (m, 7H)

Reference Example 3

10,11-Dihydro-5H-dibenzo[a,d]cyclohepten-5-carboxylic acid

The similar procedures as in Example 54 were repeated except using 5.50 g of 10,11-dihydro-5H-dibenzo[a,d]cyclohepten-5-carbonitrile in place of 9-bromo-6,11dihydrodibenz[b,e]oxepin-11-carbonitrile to obtain 2.43 g of 10,11-dihydro-5H-dibenzo[a,d]cyclohepten-5-carboxylic acid.

Melting Point: 197°–199.5° C.

Reference Example 4

10,11-Dihydro-3-methyl-5H-dibenzo[a,d]cyclohepten-5-carboxylic acid.

The similar procedures as in Example 50 were repeated except using 14.4 g of 10,11-dihydro-3-methyl-5H-dibenzo[a,d]cyclohepten-5-one in place of 6,11-dihydro-2-iododibenz[b,e]oxepin-11-one to obtain 1.62 g of 10,11-dihydro-3-methyl-5H-dibenzo[a,d]cyclohepten-5-carboxylic acid.

Melting Point: 185°–186° C.

Reference Example 5

2-Bromo-10,11-dihydro-5H-dibenzo[a,d]cyclohepten-5-carboxylic acid

The similar procedures as in Example 54 were repeated except using 2.70 g of 2-bromo-10,11-dihydro-5H-dibenzo[a,d]cyclohepten-5-carbonitrile in place of 9-bromo-6,11-dihydrodibenz[b,e]oxepin-11-carbonitrile to obtain 0.93 g of 2-bromo-10,11-dihydro-5H-dibenzo[a,d]cyclohepten-5-carboxylic acid.

Melting Point: 129°–131° C.

Reference Example 6

5H-Dibenzo[a,d]cyclohepten-5-carboxylic acid

The similar procedures as in Example 54 were repeated except using 3.48 g of 5H-dibenzo[a,d]cyclohepten-5-carbonitrile in place of 9-bromo-6,11-dihydrodibenz[b,e]oxepin-11-carbonitrile to obtain 2.45 g of 5H-dibenzo[a,d]cyclohepten-5-carboxylic acid.

Melting Point: 244°–245° C.

Preparation Example 1 Tablet

A tablet comprising the following composition is prepared in a conventional manner.

| Compound 2 | 100 mg |
|---|---|
| Lactose | 60 mg |
| Potato starch | 30 mg |
| Polyvinyl alcohol | 2 mg |
| Magnesium stearate | 1 mg |
| Tar pigment | trace |

Preparation Example 2 Powder

A powder comprising the following composition is prepared in a conventional manner.

| Compound 3 | 150 mg |
|---|---|
| Lactose | 280 mg |

What is claimed is:

1. A tricyclic compound represented by formula (I);

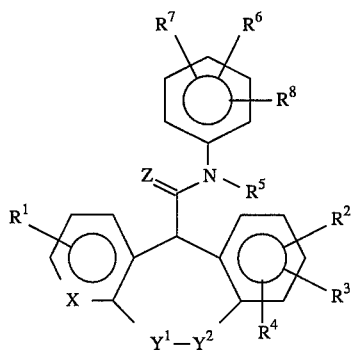

wherein each of $R^1$, $R^2$, $R^3$ and $R^4$ independently represents hydrogen, C1-6 alkyl, C1-6 alkoxy, C1-6 alkylthio, amino, C1-6 alkylamino, halogenated C1-6 alkyl, halogenated C1-6 alkoxy, halogen, nitro, cyano, carboxy, C1-6 alkoxycarbonyl, hydroxymethyl, $CR^9R^{10}CO_2R^{11}$ (wherein each of $R^9$, $R^{10}$ and $R^{11}$ independently represents hydrogen or C1-6 alkyl) or $CONR^{12}R^{13}$ (wherein each of $R^{12}$ and $R^{13}$ independently represents hydrogen or C1-6 alkyl); $R^5$ represents hydrogen or C1-6 alkyl; each of $R^6$, $R^7$ and $R^8$ independently represents hydrogen, C1-6 alkyl, hydroxy, C1-6 alkoxy, C1-6 alkanoyloxy, C1-6 alkylthio, thiocyanate or halogen; X represents CH or N; $Y^1$-$Y^2$ represents [$CH_2$—O, $CH_2$—S(O)$_n$, (wherein n represents 0, 1, or 2,)]$CH_2CH_2$, or CH=CH [or $CON(R^{14})$ (wherein $R^{14}$ represents hydrogen or C1-6 alkyl)] and Z represents oxygen or sulfur; or a pharmaceutically acceptable salt thereof.

2. The tricyclic compound as claimed in claim 1, wherein X represents CH.

3. The tricyclic compound as claimed in claim 2, wherein Z represents oxygen.

4. The tricyclic compound as claimed in claim 3, wherein $R^5$ represents hydrogen.

5. The tricyclic compound as claimed in claim 4, wherein one of $R^6$, $R^7$ and $R^8$ represents C1-6 alkyl, hydroxy, C1-6 alkoxy, C1-6 alkanoyloxy, C1-6 alkylthio, thiocyanato or halogen.

6. The tricyclic compound as claimed in claim 5, wherein one of $R^2$, $R^3$ and $R^4$ represents C1-6 alkyl, C1-6 alkoxy, C1-6 alkylthio, amino, C1-6 alkylamino, halogenated C1-6 alkyl, halogenated C1-6 alkoxy, halogen, nitro, cyano, carboxy, C1-6 alkoxycarbonyl, hydroxymethyl, $CR^9R^{10}CO_2R^{11}$ (wherein each of $R^9$, $R^{10}$ and $R^{11}$ independently represents hydrogen or C1-6 alkyl) or $CONR^{12}R^{13}$ (wherein each of $R^{12}$ and $R^{13}$ independently represents hydrogen or C1-6 alkyl).

7. The tricyclic compound as claimed in claim 6, wherein $R^1$ represents hydrogen.

8. 10,11-Dihydro-N-(2,6-diisopropylphenyl)-3-methyl-5H-dibenz[a,d]cyclohepten-5-carboxamide.

9. 2-Bromo-10, 11-dihydro-N-(2,6-diisopropylphenyl)-5H-dibenz[a,d]cyclohepten-5-carboxamide.

10. A pharmaceutical composition comprises phermaceutically acceptable carrier and as active ingredient, effective amount of the compound as defined by claim 1.

11. The tricyclic compound as claimed in claim 1, provided that when $Y^1$-$Y^2$ represents $CH_2$-$CH_2$ then (i) each of $R^6$, $R^7$ and $R^8$ independently represents hydrogen, hydroxy, C1-6 alkoxy, C1-6 alkanoyloxy, C1-6 alkylthio, thiocyanate or halogen; or (ii) one of $R^6$, $R^7$ and $R^8$ represents hydrogen, one of the remaining two groups represents 2-isopropyl and the third group represents 6-isopropyl.

* * * * *

UNITED STATES PATENT AND TRADEMARK OFFICE
CERTIFICATE OF CORRECTION

PATENT NO. : 5,478,835

DATED : December 26, 1995

INVENTOR(S): TOSHIAKI KUMAZAWA ET AL.          Page 1 of 4

It is certified that error appears in the above-identified patent and that said Letters Patent is hereby corrected as shown below:

COLUMN 1

Line 6, "No. 5,540,807" should read --No. 5,340,807--.

COLUMN 3

Line 16, "lo" should be deleted.

COLUMN 4

Form (II), " 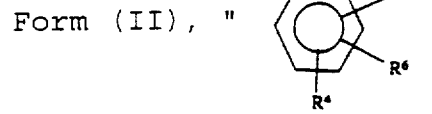 " should read -- 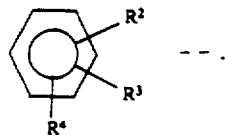 --.

COLUMN 8

Line 1, "$y^1$-$y^2$" should read --$Y^1$-$Y^2$--.

COLUMN 15

Line 43, "[14C]" should read --[$^{14}$C]--.

UNITED STATES PATENT AND TRADEMARK OFFICE
CERTIFICATE OF CORRECTION

PATENT NO. : 5,478,835

DATED : December 26, 1995

INVENTOR(S): TOSHIAKI KUMAZAWA ET AL.

It is certified that error appears in the above-identified patent and that said Letters Patent is hereby corrected as shown below:

COLUMN 16

Table 4, "21" should read --24--.
    Line 39, "made" should read --given---.

COLUMN 17

Line 62, "Under" should read --under--.

COLUMN 18

Line 28, "202 (s,6H)," should read --2.02 (s,6H),--.
    Line 54, "cm):" should read --$cm^{-1}$):--.

COLUMN 19

Line 34, "CDCl3):" should read --$CDCl_3$):--.

COLUMN 31

Line 9, "acidacetic" should read --acid-acetic--.

COLUMN 32

Line 26, "9-bromo6," should read --9-bromo-6,--.

UNITED STATES PATENT AND TRADEMARK OFFICE
CERTIFICATE OF CORRECTION

PATENT NO. : 5,478,835

DATED : December 26, 1995

INVENTOR(S) : TOSHIAKI KUMAZAWA ET AL.

It is certified that error appears in the above-identified patent and that said Letters Patent is hereby corrected as shown below:

COLUMN 34

Line 67, "AD" should read --AD.--.

COLUMN 35

Line 14, "oxepine" should read --oxypin--.
    Line 66, "type," should read --AB type,--.

COLUMN 36

Line 9, "9-bromo6," should read --9-bromo-6,--.
    Line 12, "(KBr tablet: cm$^-$)" should read
        --(KBr tablet: cm$^{-1}$)--.
    Line 26, "11dihydrod-" should read --11-dihydrod- --.
    Line 42, "9-bromo6," should read --9-bromo-6,--.

COLUMN 39

Line 3, "(2,6-diisorpopylphenyl)" should read
        --(2,6-diisopropylphenyl)--.
    Line 57, "Methyl" should be deleted.
    Line 58, "6,11-dihydro-" should read
        --"Methyl 6,11-dihydro- --.

UNITED STATES PATENT AND TRADEMARK OFFICE
CERTIFICATE OF CORRECTION

PATENT NO. : 5,478,835

DATED : December 26, 1995

INVENTOR(S) : TOSHIAKI KUMAZAWA ET AL.

It is certified that error appears in the above-identified patent and that said Letters Patent is hereby corrected as shown below:

COLUMN 43

Line 1, "$[\alpha]_D^{20}=92.35°$" shold read --$[\alpha]_D^{20}=-92.35°$--.
Line 51, "$CDC_3$):" should read --$CDCl_3$):

COLUMN 47

Line 24, "formula (I);" should read --formula (I):--.

Signed and Sealed this

Ninth Day of July, 1996

Attest:

BRUCE LEHMAN

Attesting Officer

Commissioner of Patents and Trademarks